(12) United States Patent
Appenzeller et al.

(10) Patent No.: US 10,004,603 B2
(45) Date of Patent: Jun. 26, 2018

(54) BONE IMPLANT

(71) Applicant: DePuy Synthes Products, Inc., Raynham, MA (US)

(72) Inventors: Andreas Appenzeller, Oberdorf (CH); Daniel Fluri, Oberdorf (CH)

(73) Assignee: DePuy Synthes Products, Inc., Raynham, MA (US)

( * ) Notice: Subject to any disclaimer, the term of this patent is extended or adjusted under 35 U.S.C. 154(b) by 920 days.

(21) Appl. No.: 13/832,518

(22) Filed: Mar. 15, 2013

(65) Prior Publication Data

US 2014/0058510 A1    Feb. 27, 2014

Related U.S. Application Data

(60) Provisional application No. 61/692,673, filed on Aug. 23, 2012, provisional application No. 61/710,830, filed on Oct. 8, 2012.

(51) Int. Cl.
*A61B 17/80* (2006.01)
*A61F 2/28* (2006.01)

(52) U.S. Cl.
CPC .............. *A61F 2/28* (2013.01); *A61B 17/80* (2013.01); *A61B 17/809* (2013.01); *A61B 17/8061* (2013.01); *A61B 17/8085* (2013.01)

(58) Field of Classification Search
CPC ... A61B 17/82; A61B 17/809; A61B 17/8057; A61B 17/842; A61B 17/8085; A61B 17/8014; A61B 17/8004; A61B 17/823; A61B 17/826

USPC ................... 606/280–299, 902–906
See application file for complete search history.

(56) References Cited

U.S. PATENT DOCUMENTS

| | | | |
|---|---|---|---|
| 4,429,690 A | 2/1984 | Angelino-Pievani | |
| 4,467,793 A | 8/1984 | Ender | |
| 5,281,225 A | 1/1994 | Vicenzi | |
| 5,324,307 A | 6/1994 | Jarrett et al. | |
| 5,725,532 A | 3/1998 | Shoemaker | |
| 5,766,176 A | 6/1998 | Duncan | |
| 5,913,896 A | 6/1999 | Boyle et al. | |
| 6,203,545 B1 | 3/2001 | Stoffella | |
| 6,306,136 B1 | 10/2001 | Baccelli | |
| 6,436,099 B1* | 8/2002 | Drewry ............. | A61B 17/7022 606/300 |

(Continued)

FOREIGN PATENT DOCUMENTS

| | | |
|---|---|---|
| CA | 2626694 C | 8/2011 |
| CN | 1337864 | 2/2002 |

(Continued)

OTHER PUBLICATIONS

U.S. Appl. No. 13/974,310, filed Aug. 23, 2013, Appenzeller et al.

(Continued)

*Primary Examiner* — Matthew Lawson
(74) *Attorney, Agent, or Firm* — Baker & Hostetler LLP

(57) ABSTRACT

A bone implant that is elongate along a longitudinal axis includes an implant body including first and second side wire segments that are spaced from each other so as to define at least one apertures extending through the implant body. The at least one aperture is configured to receive a bone fixation element so as to secure the bone implant to bone.

27 Claims, 15 Drawing Sheets

(56) References Cited

U.S. PATENT DOCUMENTS

| | | | |
|---|---|---|---|
| 6,506,191 | B1 | 1/2003 | Joos |
| 6,558,388 | B1 | 5/2003 | Bartsch et al. |
| 7,776,076 | B2 | 8/2010 | Grady et al. |
| 8,118,846 | B2 | 2/2012 | Leither et al. |
| 8,172,884 | B2 | 5/2012 | Bouman |
| 8,343,152 | B2 | 1/2013 | Gonzalez-Hernandez |
| 2003/0023241 | A1 | 1/2003 | Drewry |
| 2003/0153918 | A1 | 8/2003 | Putnam et al. |
| 2004/0102776 | A1 | 5/2004 | Huebner |
| 2004/0236170 | A1 | 11/2004 | Kim |
| 2005/0101961 | A1 | 5/2005 | Huebner et al. |
| 2005/0136764 | A1* | 6/2005 | Sherman ........... A61B 17/7059 442/103 |
| 2005/0261688 | A1 | 11/2005 | Grady, Jr. et al. |
| 2006/0009771 | A1 | 1/2006 | Orbay et al. |
| 2006/0189992 | A1 | 8/2006 | Medoff |
| 2006/0235399 | A1 | 10/2006 | Carls et al. |
| 2006/0235400 | A1 | 10/2006 | Schneider |
| 2006/0276793 | A1 | 12/2006 | Berry |
| 2007/0173834 | A1 | 7/2007 | Thakkar |
| 2008/0065074 | A1 | 3/2008 | Yeung et al. |
| 2008/0188899 | A1 | 8/2008 | Bottlang et al. |
| 2008/0269745 | A1 | 10/2008 | Justin |
| 2008/0281363 | A1* | 11/2008 | Ullman ............ A61B 17/6408 606/329 |
| 2009/0069851 | A1* | 3/2009 | Gillard ............ A61B 17/1684 606/280 |
| 2009/0264936 | A1 | 10/2009 | Gonzalez-Hernandez et al. |
| 2010/0036430 | A1 | 2/2010 | Hartdegen et al. |
| 2010/0063549 | A1* | 3/2010 | Orbay ............ A61B 17/1739 606/281 |
| 2010/0305569 | A1 | 12/2010 | Leuenberger et al. |
| 2011/0009912 | A1* | 1/2011 | Gonzalez-Hernandez A61B 17/7208 606/328 |
| 2011/0257685 | A1 | 10/2011 | Hay et al. |
| 2011/0270312 | A1 | 11/2011 | Assell et al. |
| 2011/0282393 | A1 | 11/2011 | Gerlach et al. |
| 2012/0004690 | A1* | 1/2012 | Gonzalez-Hernandez A61B 17/8695 606/305 |
| 2012/0109128 | A1 | 5/2012 | Frigg |
| 2012/0136396 | A1 | 5/2012 | Baker et al. |
| 2012/0239036 | A1 | 9/2012 | Voisard |
| 2012/0330365 | A1 | 12/2012 | Lin et al. |
| 2014/0039561 | A1* | 2/2014 | Weiner .................. A61B 17/80 606/282 |
| 2014/0058391 | A1 | 2/2014 | Appenzeller et al. |
| 2014/0058455 | A1 | 2/2014 | Appenzeller et al. |
| 2014/0058510 | A1 | 2/2014 | Appenzeller et al. |
| 2015/0018889 | A1 | 1/2015 | Schneider |
| 2015/0223853 | A1 | 8/2015 | Appenzeller et al. |

FOREIGN PATENT DOCUMENTS

| | | |
|---|---|---|
| CN | 1482890 A | 3/2004 |
| CN | 1631325 | 6/2005 |
| CN | 1694653 A | 11/2005 |
| CN | 1911454 A | 2/2007 |
| CN | 1988854 | 6/2007 |
| CN | 2922820 | 7/2007 |
| CN | 102421383 A | 4/2012 |
| CN | 102458284 | 5/2012 |
| CN | 102470197 A | 5/2012 |
| DE | 202005019277 | 2/2006 |
| EP | 0401650 | 12/1990 |
| EP | 0743045 | 11/1996 |
| EP | 0873718 | 10/1998 |
| EP | 0882431 | 12/1998 |
| EP | 2887894 A1 | 7/2015 |
| FR | 2722545 | 1/1996 |
| FR | 2728155 | 6/1996 |
| JP | 57-081333 A | 5/1982 |
| JP | 2002-541968 A | 12/2002 |
| JP | 2006-506197 A | 2/2006 |
| JP | 2007-083046 A | 4/2007 |
| JP | 2007-514507 A | 6/2007 |
| JP | 2008-535561 A | 9/2008 |
| JP | 2010-517673 A | 5/2010 |
| JP | 2011-500166 A | 1/2011 |
| JP | 2011-529748 A | 12/2011 |
| JP | 2015-526204 A | 9/2015 |
| RU | 2133593 C1 | 7/1999 |
| RU | 2171651 C1 | 8/2001 |
| RU | 2245685 C2 | 2/2005 |
| RU | 2253395 C1 | 6/2005 |
| RU | 108948 U1 | 10/2011 |
| SU | 1367961 A1 | 1/1988 |
| TW | 201219004 A | 5/2012 |
| TW | 201221258 A | 6/2012 |
| WO | WO 87/02572 | 5/1987 |
| WO | WO 98/33448 | 8/1998 |
| WO | WO 2012/103164 | 8/2012 |
| WO | 2014/031935 A1 | 2/2014 |

OTHER PUBLICATIONS

International Patent Application No. PCT/US2013/056345: International Search Report dated Oct. 23, 2013, 10 pages.
International Patent Application No. PCT/US2013/056367: International Search Report dated Oct. 23, 2013, 10 pages.
International Patent Application No. PCT/US2013/056348: Invitation to Pay Additional Fees dated Oct. 23, 2013, 6 pages.
International Patent Application No. PCT/US2013/056374: International Search Report dated Nov. 5, 2013, 10 pages.
International Patent Application No. PCT/US2013/056348: International Search Report dated Jan. 17, 2014, 16 pages.

* cited by examiner

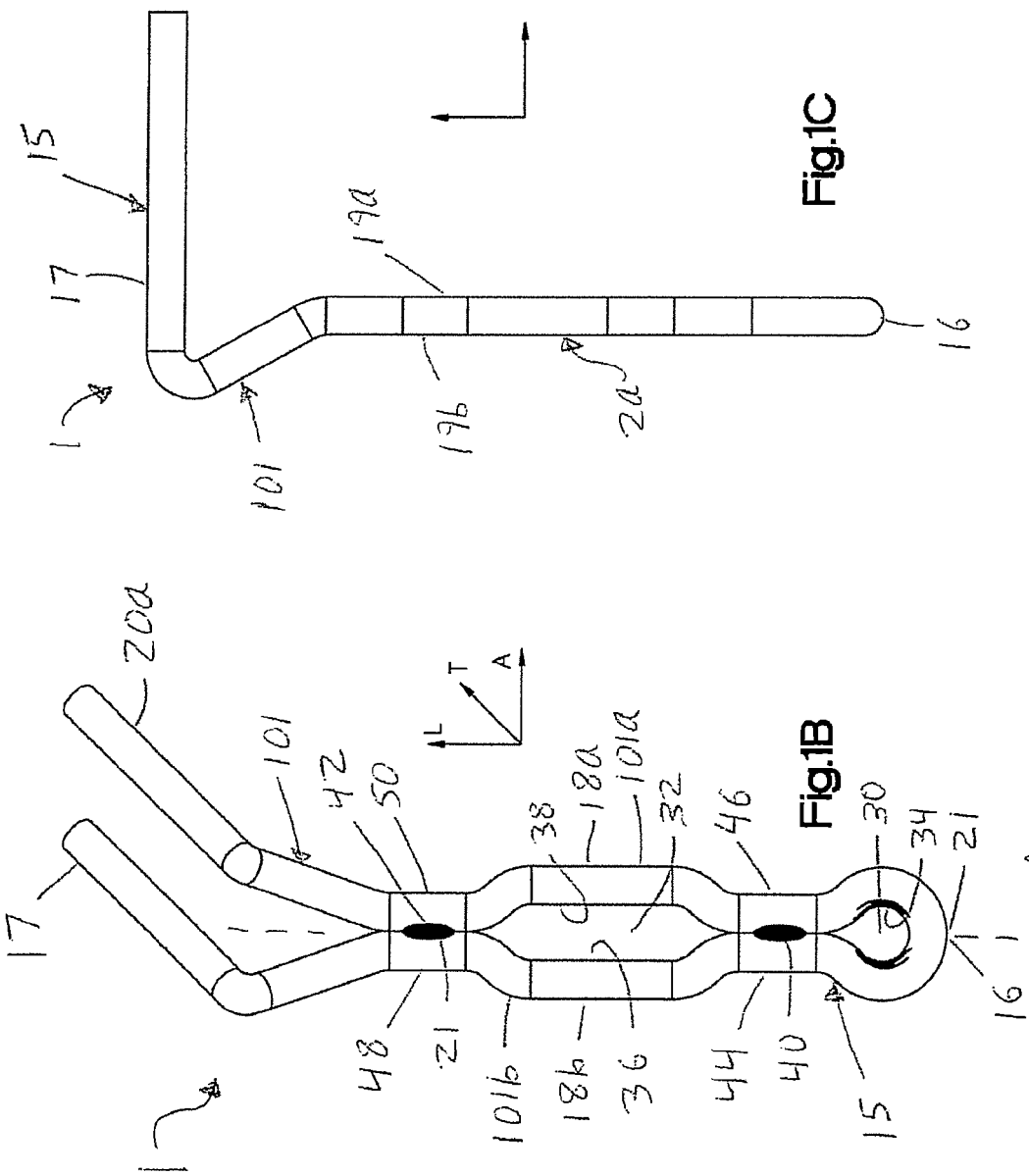

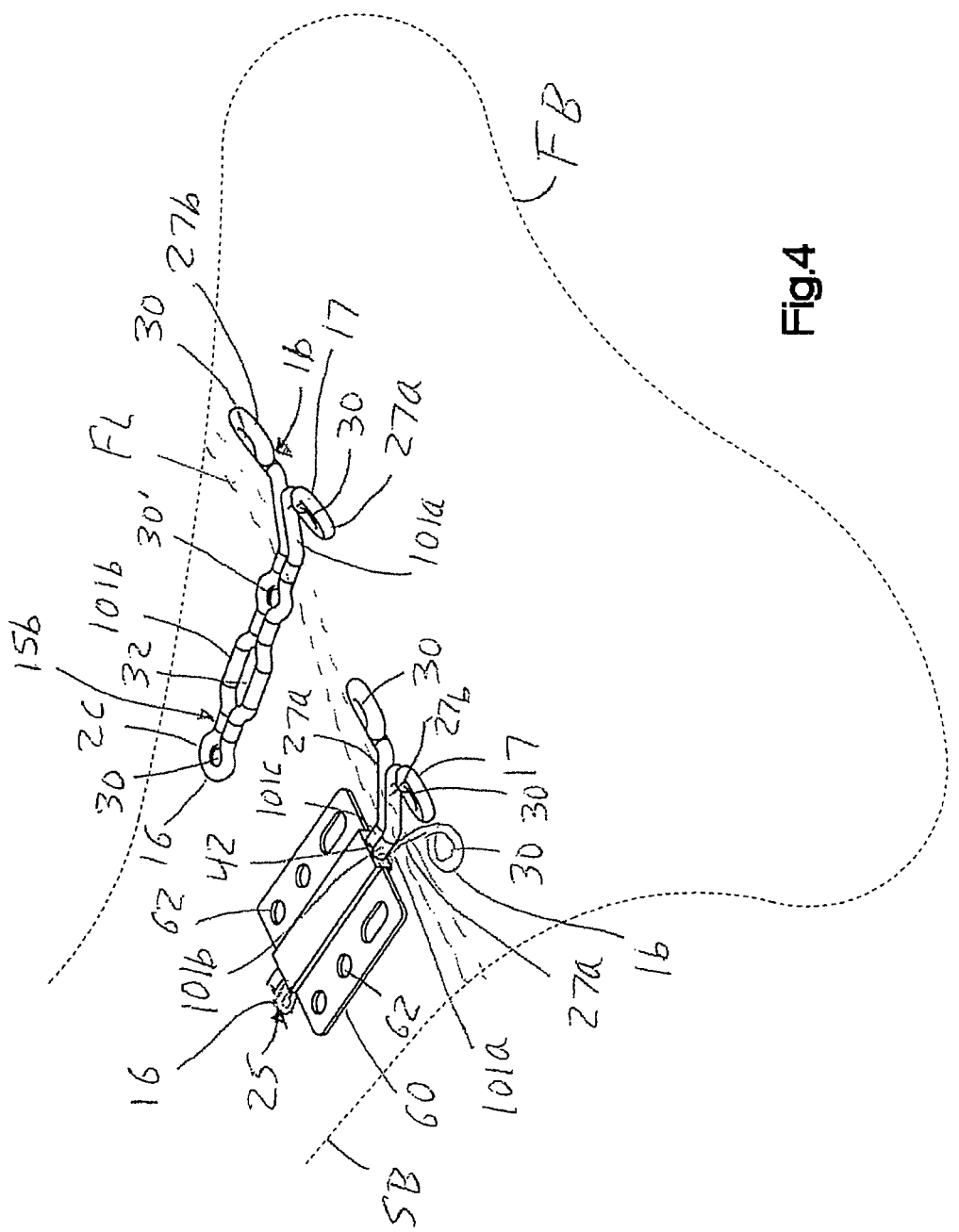

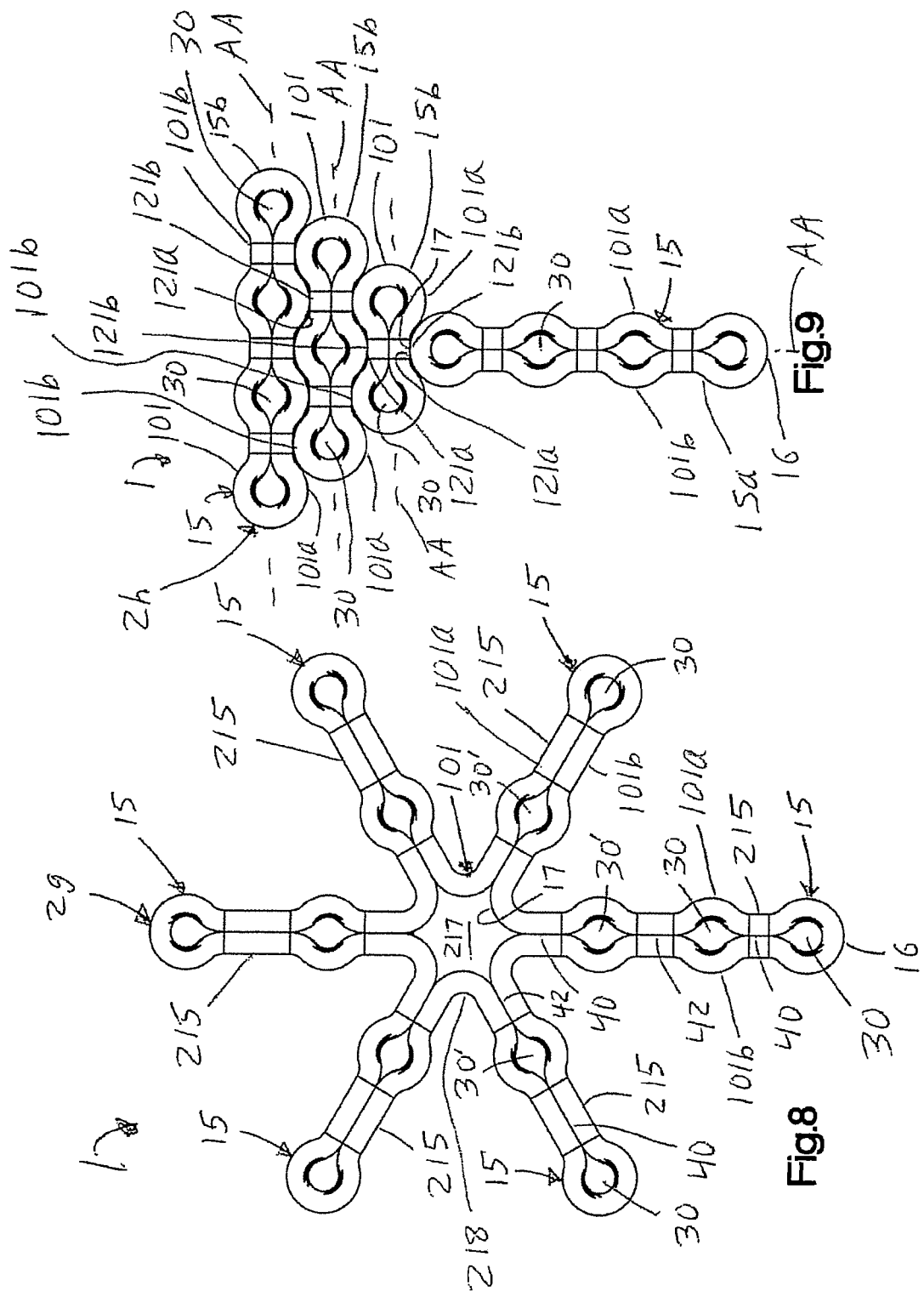

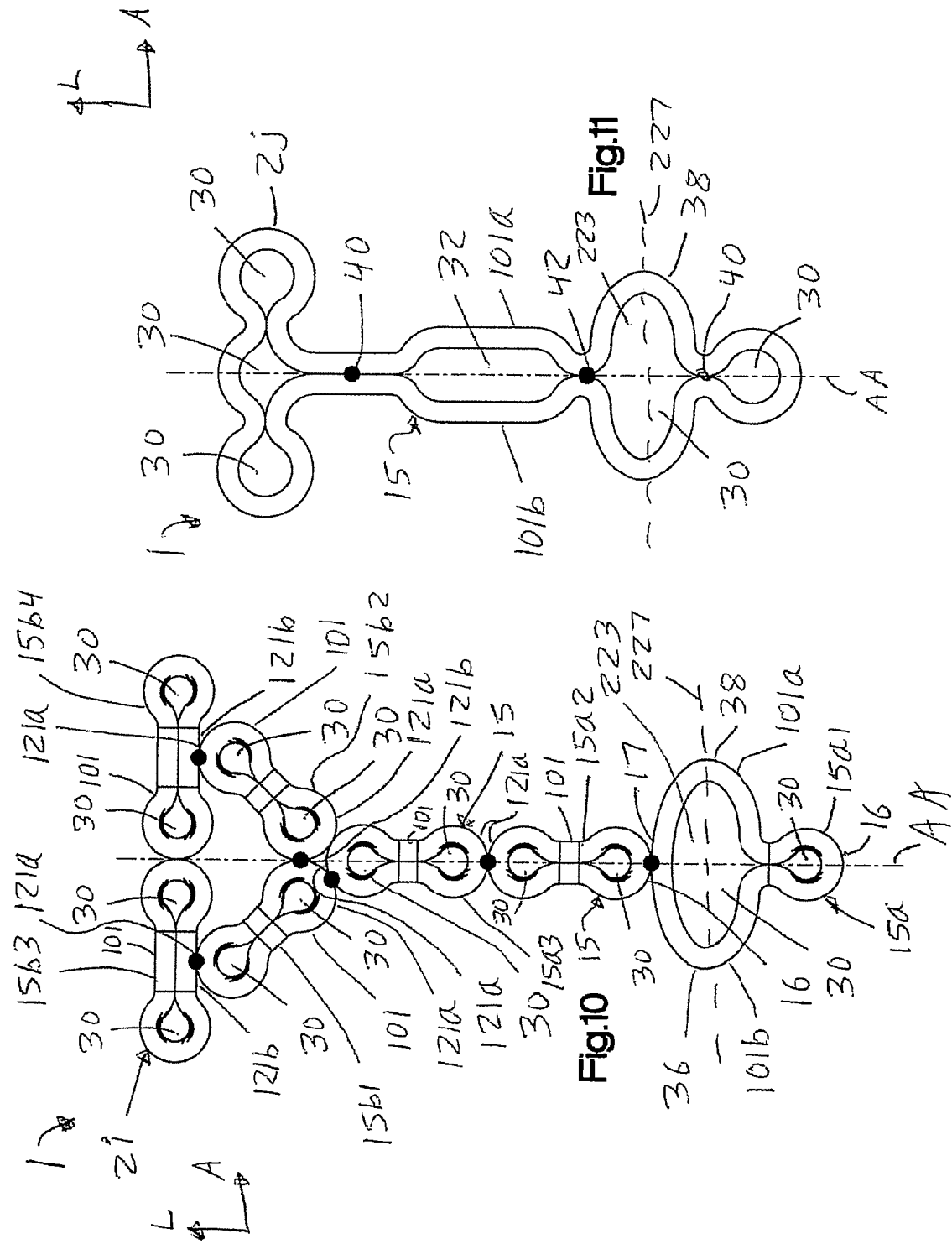

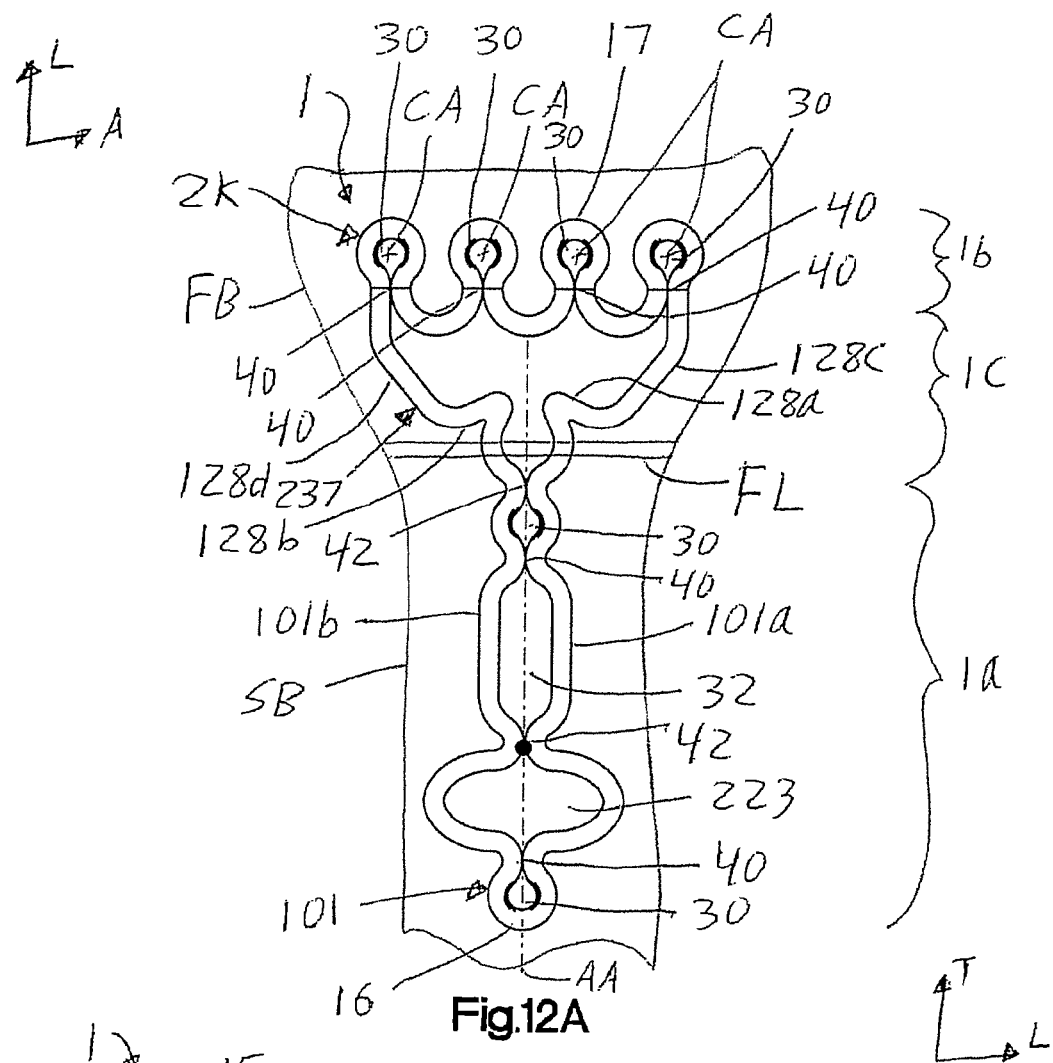
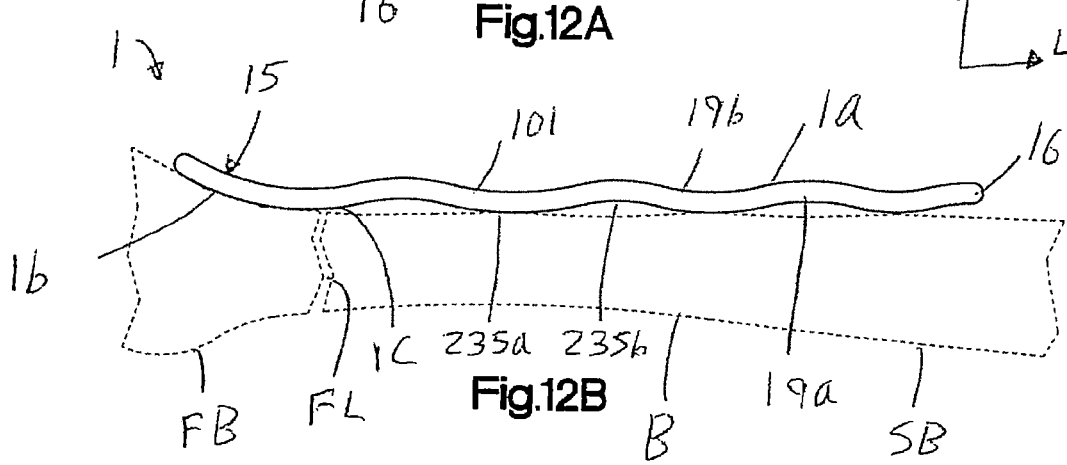
Fig.12A
Fig.12B

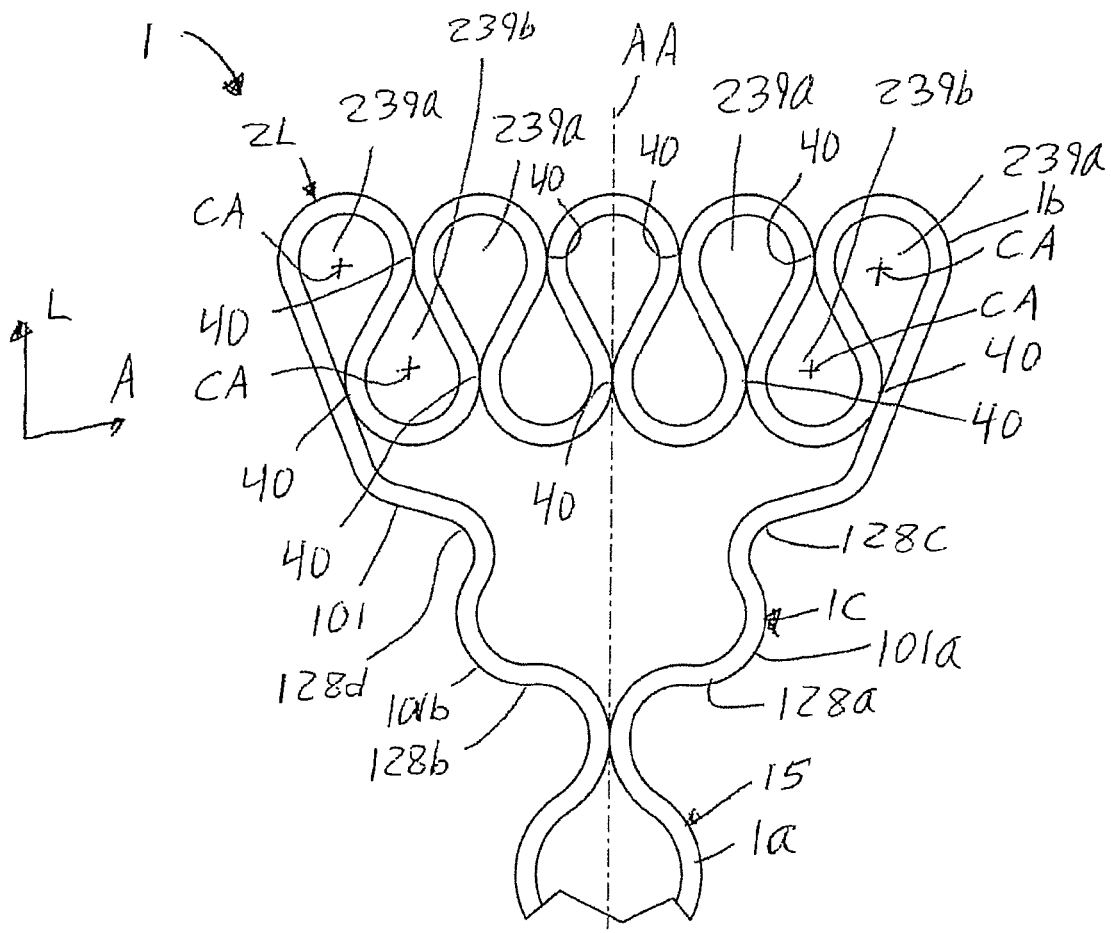
Fig.13A
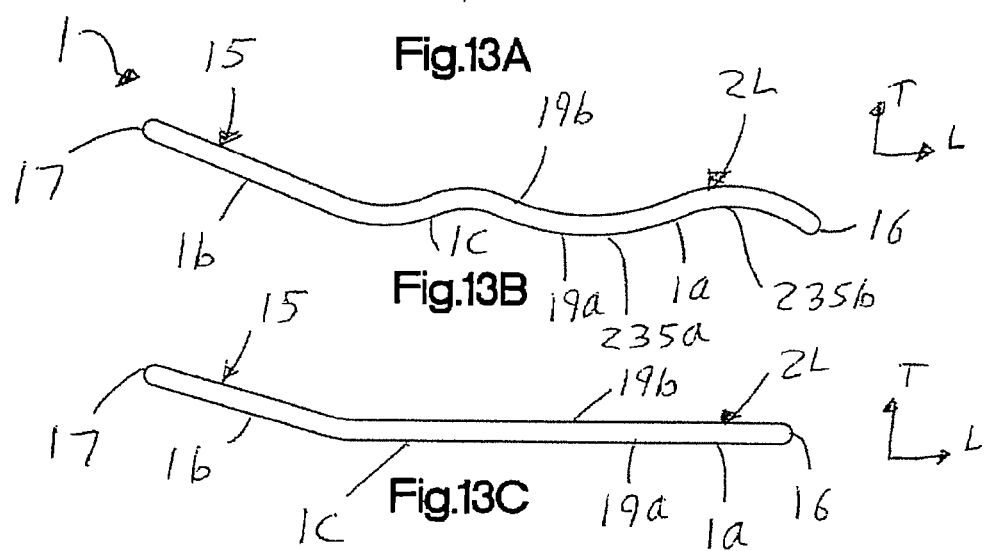
Fig.13B
Fig.13C

BONE IMPLANT

CROSS REFERENCE TO RELATED APPLICATIONS

This claims the benefit of U.S. Provisional Patent Application Ser. No. 61/692,673 filed Aug. 23, 2012, and further claims the benefit of U.S. Provisional Patent Application Ser. No. 61/710,830 filed Oct. 8, 2012, the disclosure of each of which is hereby incorporated by reference as if set forth in its entirety herein.

FIELD OF THE DISCLOSURE

The present disclosure relates to bone implants, bone implant assemblies, bone fixation elements, methods of manufacturing bone implants, and methods of supporting bone healing.

BACKGROUND

In the 1950s the AO (Arbeitsgemeinschaft für Osteosynthesefragen) Foundation was set up to research the use of bone implants in bone healing. The AO Foundation established four principles for the development of bone implants suitable for supporting bone healing. The AO principles are:
  Anatomic reduction of the fracture fragments, particularly in joint fractures;
  Stable fixation to ensure proper healing of the fracture allowing surrounding tissue to move and strengthen;
  A traumatic surgical technique to preserve the blood supply to the bone fragments and soft tissue; and
  Early, pain-free mobilization returning the patient to function as soon as possible.

Following these well-established principles many examples and types of bone implants, such as bone plates, intramedullary nails, etc., have been developed and are used in bone healing. These bone implants are often made of metal or metallic material and are commonly fabricated as a single piece having a planar or a cylindrical shape. The bone implants are often manufactured using a number of manufacturing processes including milling, cutting, drilling, hole forming, thread forming, etc. Each process may involve different instrumentation, may take a certain amount of time and can result in a certain amount of waste material.

There is thus a need to simplify manufacturing processes and reduce waste material created during the fabrication of bone implants conforming to the AO principles.

SUMMARY

In accordance with one embodiment, a bone implant can be elongate along a central axis and configured to attach to first and second bone fragments separated by a bone fracture. The bone implant can include an implant body including a wire that defines first and second side walls, respectively, and at least one aperture that extends through the implant body between the first and second side walls. The aperture can be configured to receive a bone fixation element so as to attach the bone implant to bone. The first and second side walls can extend continuously from a first end of the aperture to a second end of the aperture spaced from the first end of the aperture along the central axis, such that the first and second side walls define the aperture. The first and second side walls can be spaced from each other a first distance along a direction that is perpendicular to the central axis at the aperture, and second and third distances, respectively, at the first and second ends. Each of the second and third distances can be less than the first distance.

In a first aspect of the present disclosure there is provided a bone implant. The bone implant has a wire. The wire may define an aperture for receiving a bone fixation means The wire may have a first portion fixed to a second portion at an abutment point where the first and second portions contact each other. The wire may be selected to stably fix a bone across a fracture location.

The abutment point may be located in a region adjacent an aperture. The aperture may be defined by the wire or may be punched through the wire.

The bone implant may comprise a plurality of apertures for receiving a fixation means. At least one abutment point may be located adjacent each one of the plurality of apertures.

The aperture or apertures may be one or a combination apertures types chosen from threaded, non-threaded, variable angle, compression, locking-compression and combihole.

In a second aspect of the present disclosure there is provided a bone implant. The bone implant has a wire shaped to define a threaded aperture.

In a third aspect of the present disclosure there is provided a bone implant. The bone implant has a wire having portions defining an aperture. The aperture may have a central axis and the portions of the wire defining the aperture may lie in a plane perpendicular to the central axis.

In a fourth aspect of the present disclosure, the bone implant consists of a wire defining the shape of the implant and an aperture for receiving a fixation means therethrough.

The aperture or apertures may be threaded.

The aperture of the bone implant of any of the first, second, third and fourth aspects may be arranged to lock a fixation means therein. The aperture may be threaded for locking a fixation means therein.

The bone implant of any of the first, second, third and fourth aspects may have a longitudinal axis and an implant plane perpendicular to the longitudinal axis. The aperture of the bone implant may have a variable angle aperture adapted to lock a fixation means at variable angles relative to the implant plane. The variable angle aperture has a central axis passing therethrough, the central axis may be orientated at a first angle relative to the implant plane. The wire defining the variable angle aperture may be manipulatable from a first configuration to a second configuration to orientate the angle of the central axis relative to the implant plane to a second angle for varying the angle at which a fixation means can be locked relative to the implant plane. The wire may be manipulatable by bending in a region adjacent the variable angle aperture. The variable angle aperture may be configured to lock a head a fixation means coaxially with the central axis.

The wire of bone implants of any of the first, second, third and fourth aspects may be fixed in a first region adjacent the screw hole where a first portion of the wire abuts a second portion of the wire.

The wire of bone implants of any of the first, second, third and fourth aspects may be fixed in a second region adjacent the screw hole where a third portion of the wire abuts a fourth portion of the wire. The second region may be different to the first region.

The wire of the bone implant of any of the first, second, third and fourth aspects may have a suitable rigidity. The rigidity of the wire may be chosen to ensure that the bone implant achieves a stable fixation.

The bone implant of any of the first, second, third and fourth aspects may have a plurality of apertures. The plurality of apertures may be of the same type. The plurality of apertures may feature a multitude of different types of aperture. The plurality of apertures may have at least a first and at least a second type of aperture. The types of aperture may be one of threaded, non-threaded, variable angle, compression and combi-hole.

The bone implant of any of the first, second, third and fourth aspects may be formed by bending wire in a predetermined manner. The bone implant may be formed by bending a first wire in a predetermined manner and by bending a second wire around at least a first region of the first wire and fixing the second wire to the first wire in the first region.

The wire of bone implants of any of the first, second, third and fourth aspects may be fixed together by any suitable fixation process. Suitable processes may include, but are not limited to, welding, gluing, bonding, soldering, pressing, twisting, crimping and clamping.

The aperture is or plurality of apertures of bone implants of any of the first, second, third and fourth aspects may be defined by a first portion of a wire and a second portion of a wire. The first and second portions may be located on the same wire. The first and second portions may be located on separate distinct wires. At least one aperture may be defined by first and second portions of the same wire and at least one aperture may be defined by first and second portions of different wires.

The aperture is or plurality of apertures of bone implants of any of the first, second, third and fourth aspects may have a further wire portion fixed to a portion of the wire defined aperture to strength the aperture.

The aperture is or plurality of apertures of bone implants of any of the first, second, third and fourth aspects may be defined by a hole punched in the wire.

The wire of bone implants of any of the first, second, third and fourth aspects may define a circular aperture.

The wire of bone implants of any of the first, second, third and fourth aspects may define an elongate aperture.

The apertures of bone implants of any of the first, second, third and fourth aspects may be one or a combination of circular and elongate.

The bone implant of any of the first, second, third and fourth may define at least one bone engaging prong.

The bone implant of any of the first, second, third and fourth aspects may be a bone plate or an intramedullary nail.

According to the present disclosure in a fifth aspect there is provided a fixation element having a head and a shaft, the head adapted for engagement with a wire defined aperture. The head may have a convex groove shaped according to the diameter of the wire in which it is to be inserted.

A resilient element may be arranged around the junction between the head and the shaft. The resilient element may be deformable by insertion pressure exerted on the fixation element during insertion into a wired formed aperture. The resilient element may be a circlip.

According to the present disclosure in a sixth aspect, there is provided a bone implant assembly. The bone implant assembly may have:
a bone implant comprising wire and an aperture; and
a fixation element with a head engageable with inner wall of to be locked therein.

The bone implant may be a bone implant according to any one the first, second and third aspects.

The fixation means may be one of a cortical screw, a locking screw, a variable angle locking screw, a bone pin, a rivet and a staple.

The fixation means may have a head from which a shaft extends. The head may have a groove fixedly engageable with a portion of the wire of the bone implant.

According to the present disclosure in a seventh aspect, there is provided a method of making a bone implant. The method may have the steps of:
providing a wire; and
defining a stabilization feature.

The stabilization feature might be any feature suitable for stabilizing the bone implant. For example, the stabilization feature may be one or a combination of the following:
a weld at a point where a first portion of wire abuts a second portion of wire;
an aperture; and
an aperture defined by wire lying in the same plane.

The method may involve bending the wire into a predetermined shape.

The method may involve:
bending a first wire portion according to a first predetermined shape;
bending a second wire portion according to a second predetermined shape;
arranging the first wire portion adjacent a second wire portion;
fixing the first wire portion to the second wire portion at a point where they abut each other.

The method may have the following further steps:
providing a second wire;
forming the second wire around at least a portion of the first wire; and
welding the second wire to the first wire.

The bone implant for the method may be one of a bone plate and an intramedullary nail.

According to the present disclosure in an eighth aspect, there is provided a method of supporting healing of a bone. The method may have the steps of:
Selecting a bone implant according to any one of the first, second and third aspects of the present disclosure, or a bone implant assembly according to the fourth aspect of the present disclosure; and
Performing a surgical procedure in which the bone implant is fixed to the bone.

The method may involve the step of removing the bone implant after a determination that sufficient bone healing has taken place.

The step of performing a surgical procedure may involve:
adapting a bone implant according to a fractured bone to be stabilized;
aligning the adapted plate with the fractured bone; and
stabilizing the fracture by inserting a first bone fixation element into at least a first aperture in the bone implant.

The step of adapting may involve:
adapting at least one aperture having a central axis passing therethrough by altering the angle of the central axis relative to an implant plane that lies perpendicular to a longitudinal axis of the bone implant.

The step of stabilizing the fracture may involve:
inserting the first bone fixation element through the first aperture into a first bone fragment on one side of bone fracture;
inserting a second bone fixation element through a second aperture into a second bone fragment on another side of the bone fracture;

compressing the bone fragments to achieve a reduction of the fracture;

and inserting a third fixation element to maintain the position of the first bone fragment relative to the second bone fragment during bone healing.

A BRIEF DESCRIPTION OF THE DRAWINGS

One or more embodiments of the present disclosure will now be described below with reference to the accompanying drawings, in which:

FIG. 1B is a perspective view of the bone implant illustrated in FIG. 1A;

FIG. 1C is a side elevation view of the bone implant illustrated in FIG. 1A;

FIG. 4 is a plan view of a pair of bone implants constructed in accordance with additional embodiments, show implanted on a fractured bone;

FIG. 8 is a plan view of a bone implant constructed in accordance with another embodiment;

FIG. 9 is a plan view of a bone implant constructed in accordance with another embodiment;

FIG. 10 is a plan view of a bone implant constructed in accordance with another embodiment;

FIG. 11 is a plan view of a bone implant constructed in accordance with another embodiment;

FIG. 12A is a plan view of a bone implant constructed in accordance with another embodiment, shown implanted on a fractured bone;

FIG. 12B is a side elevation view of the bone implant of FIG. 12A, shown implanted on the fractured bone;

FIG. 13A is a plan view of a bone implant constructed in accordance with another embodiment;

FIG. 13B is a side view of the bone implant illustrated in FIG. 13A;

FIG. 13C is a side view of a bone implant similar to the bone implant of FIG. 13B, but constructed in accordance with an alternate embodiment;

Figure 14A:
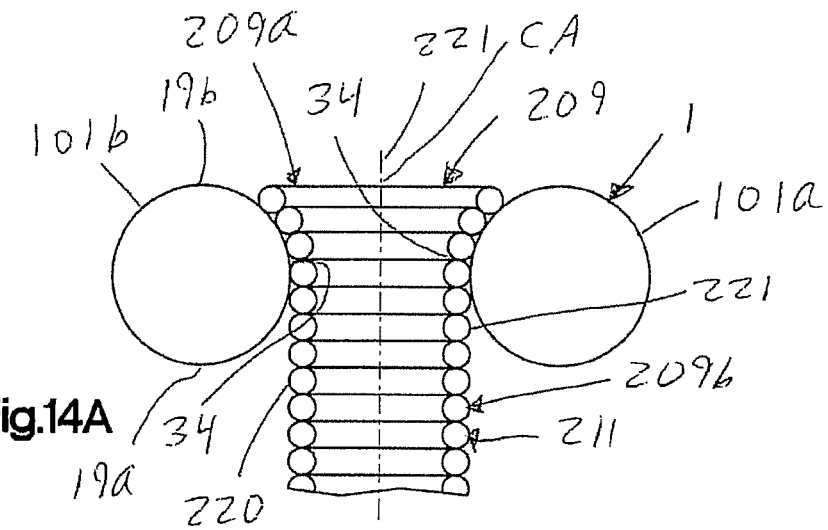
FIG. 14A is a sectional side elevation view of a bone fixation element constructed in accordance with another embodiment, the bone fixation element shown inserted into a bone implant of the present disclosure so as to secure the bone implant to bone.
Figure 14B:
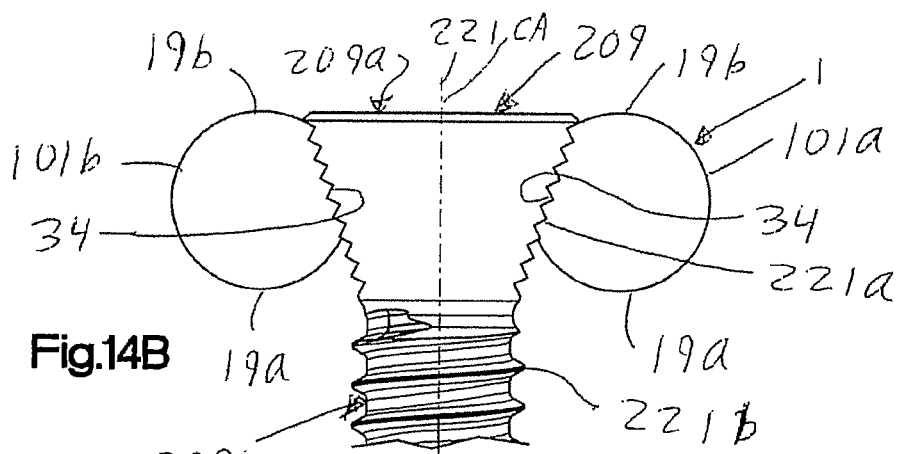
FIG. 14B is a sectional side elevation view of a bone fixation element constructed in accordance with another embodiment, the bone fixation element shown inserted into a bone implant of the present disclosure so as to secure the bone implant to bone.
Figure 14C:
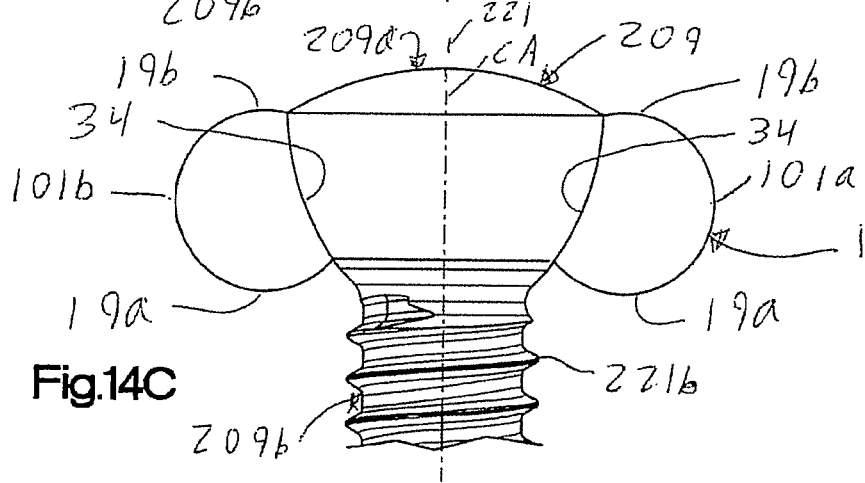
Figure 14D:
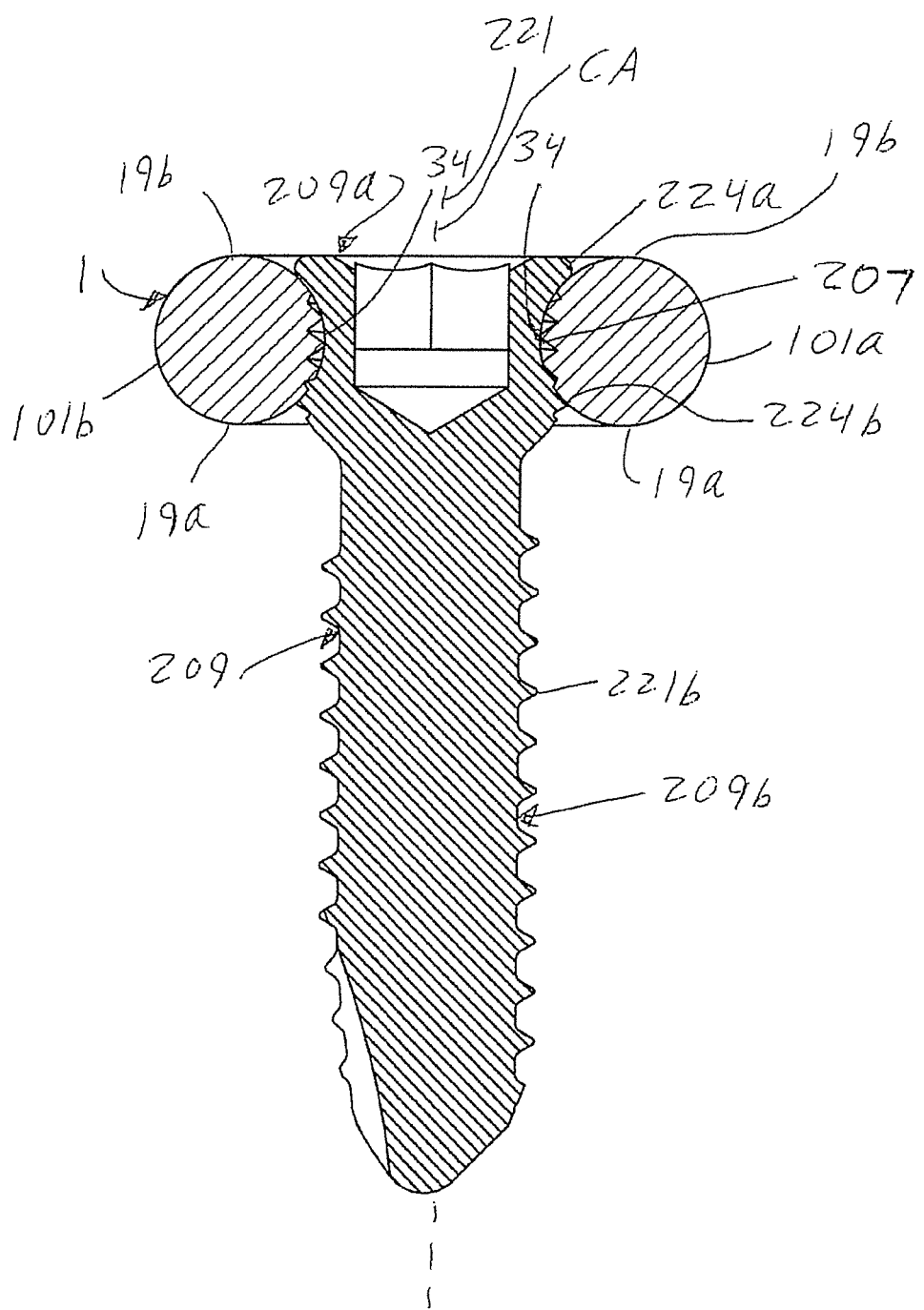

FIG. 14C is a sectional side elevation view of a bone fixation element constructed in accordance with another embodiment, the bone fixation element shown inserted into a bone implant of the present disclosure so as to secure the bone implant to bone; and FIG. 14D is a sectional side elevation view of a bone fixation element constructed in accordance with another embodiment, the bone fixation element shown inserted into a bone implant of the present disclosure so as to secure the bone implant to bone.

DETAILED DESCRIPTION OF THE PREFERRED EMBODIMENTS

The present disclosure describes various embodiments of bone implants of the present disclosure. The bone implants use wire to define various bone stabilization features, and the bone implants can be made at least partially or entirely from wire. The bone stabilization features are useable in maintaining a stable fixation of a bone fracture during bone healing. Since the bone implants use wire that is bent into a desired shape, processing steps, e.g. milling, cutting, drilling, and the like, in which bone plate material is removed during conventional bone plate manufacturing, can be avoided. Hence, bone implants of the present disclosure can be made with a reduced volume of waste material with respect to conventional bone plates.

Figure 1A:
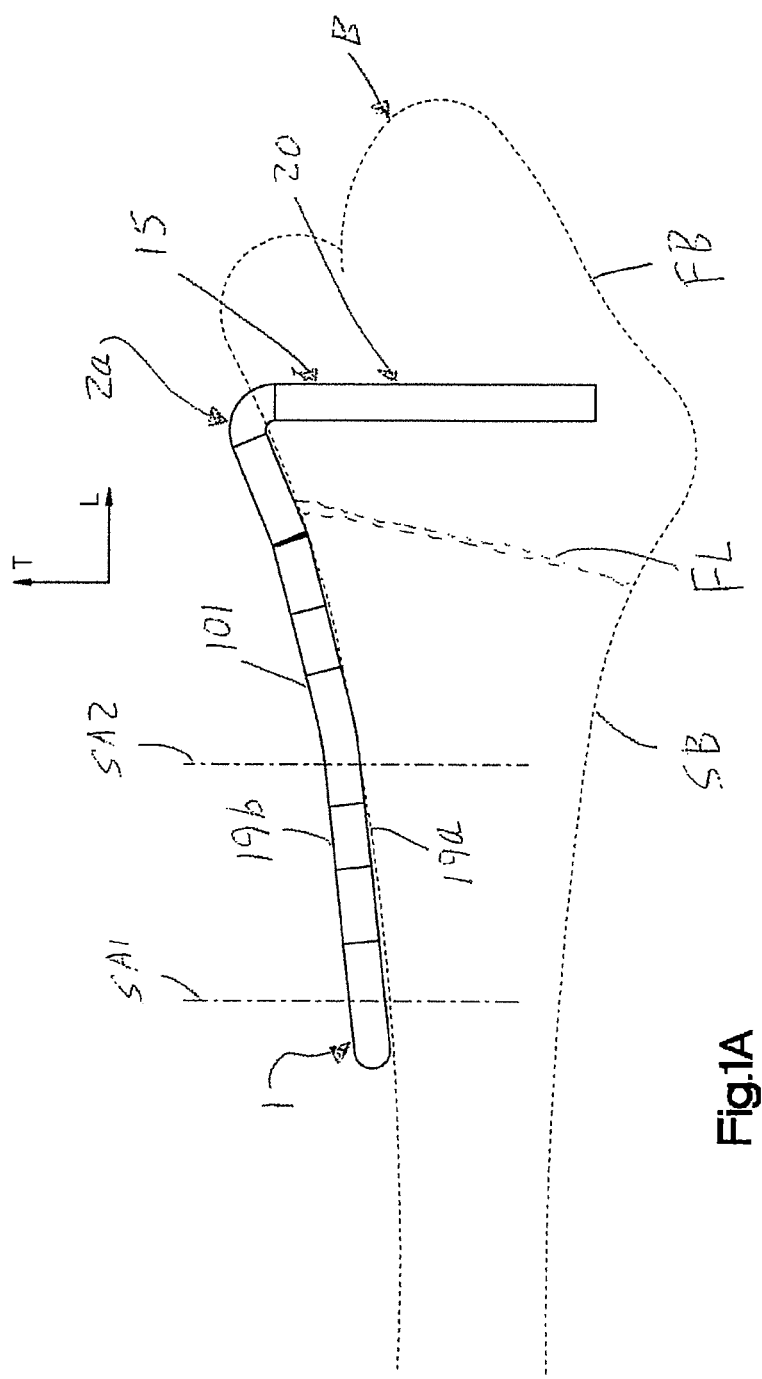
FIG. 1A is a perspective view of a bone implant constructed in accordance with one embodiment, shown implanted on a fractured bone.

Referring to FIGS. 1A-1C, a bone implant 1 is configured to stabilize a bone B that has been fractured at one or more fracture locations FL into a plurality of bone fragments, for example, a first bone fragment FB and a second bone fragment SB that is spaced from the first bone fragment FB along the central bone axis. The fracture location FL is disposed between the first bone fragment FB and the second bone fragment SB. The bone implant 1 can be configured as one or more bone plates constructed in accordance with any embodiment described herein. As illustrated in FIGS. 1A-C, the bone implant 1 can be configured as a bone plate 2, and can include an implant body 15 that is elongate substantially along a central, or longitudinal, axis AA and defines a proximal end 16, a distal end 17 spaced from the proximal end 16 along the central axis AA, and lateral sides 18a and 18b that are spaced from each other along a second direction that is angularly offset, for instance perpendicular, with respect to the central axis AA. As used herein, a proximal direction can refer to a direction that extends from the distal end 17 to the proximal end 16, and a distal direction can refer to a direction that extends from the proximal end 16 to the distal end 17. The central or longitudinal axis AA, also referred to herein as a central axis, can be straight, curved, or otherwise shaped as desired.

In accordance with one embodiment, the central axis AA can extend along a longitudinal direction L, and the lateral sides 18a and 18b can be spaced from each other along a lateral direction A that is substantially perpendicular to the longitudinal direction L. Thus, reference to the longitudinal direction L herein equally refers to the central axis AA, and vice versa, unless otherwise indicated. Further, reference to the lateral direction A herein equally refers to the second direction, and vice versa, unless otherwise indicated. The implant body 15 can further define a bone facing inner surface 19a and an opposed outer surface 19b that faces away from the bone when the implant 15 is secured onto the bone B. The bone facing surface 19a and the opposed outer surface 19b can be spaced from each other along a transverse direction T that is substantially perpendicular with respect to both the longitudinal direction L and the lateral direction A. For instance, an inner transverse direction T can refer to a direction from the outer surface 19b toward the bone facing surface 19a, and an outer transverse direction T can refer to a direction from the bone facing surface 19a toward the outer surface 19b. It will be appreciated from the description below that the bone facing surface 19a can abut and compress against the bone B, for instance when secured to the bone B with compression screws, or can be spaced from the bone B or abut the bone with limited compression, for instance when secured to the bone with locking screws.

The implant body 15 can include at least one wire 101 that defines at least one wire segment, for instance a first wire segment 101a and a second wire segment 101b, in accordance with the illustrated embodiment, that are shaped to define a bone plate. It should be appreciated that the first and second wire segments 101a and 101b can be integral and monolithic with each other, such that they form part of the wire 101. Alternatively, the first and second wire segments 101a and 101b can be separate from each other, and defined by two different respective wires. Unless otherwise indicated, reference to either or both of the first and second wire segments 101a and 101b herein refers to both the wire 101 as well as two separate wires, unless otherwise indicated. The bone implant 1, and the implants described herein, can be partially or entirely completely made of wire, which can define any size and shape as desired, and can for instance define bone fixation holes having a diameter or other cross-sectional dimension along the lateral direction of any size as desired, such as up to approximately 10 mm, for instance between and including about 6 mm and about 10 mm.

The wire segments 101a-b can be bent as desired to form the shape of the bone implant 1. The bone implant 1 can define at least one or more, such as a plurality of, necks 40 and 42 along the implant body 15 where at least one or both of the first and second wire segments 101a and 101b extend toward the central axis AA, and thus also toward the other of the first and second wire segments 101a and 101b. In accordance with one embodiment, the first and second wire segments 101a and 101b can abut each other at the necks 40 and 42, such that the necks 40 and 42 can be referred to as abutment locations. For instance, the first wire segment 101a can define a first lateral side wall 38 that, in turn, can define first and second wire portions 46 and 50, respectively. The second wire segment 101b can define a second lateral side wall 36 that can, in turn, define corresponding first and second wire portions 44 and 48, respectively.

The first wire portion 46 of the first wire segment 101a is configured to extend toward the first wire portion 44 of the second wire segment 101b so as to at least partially define the first neck 40. Thus, the first wire portion 46 can be referred to as a first necked wire portion. For instance, the first wire portion 46 can extend toward the first wire portion 44 at the neck 40 substantially along a plane that includes the longitudinal direction L and the lateral direction A. Similarly, the first wire portion 44 of the second wire segment 101b is configured to extend toward the first necked portion 46 of the first wire segment 101a so as to at least partially define the first neck 40. For instance, the first wire portion 44 can extend toward the first wire portion 46 at the neck 40 substantially along a plane that includes the longitudinal direction L and the lateral direction A. Thus, the first wire portion 44 can be referred to as a first necked wire portion. The first wire portions 44 and 46 can be spaced from each other at the first neck 40, for instance along the lateral direction A, or the first wire portions 44 and 46 can abut each other at the first neck 40, for instance at a location that is coincident with the central axis AA. It should be appreciated, of course, that the first wire portions 44 and 46 can abut each other at any location with respect to the central axis AA, for instance offset from the central axis AA along the lateral direction A. Further, in embodiments wherein the first wire portions 44 and 46 are spaced from each other, the first wire portions 44 and 46 can be spaced from each other along a select direction, for instance the lateral direction A, a distance that is less than a distance that one or more adjacent portions of the respective wire segments 101a and 101b that are adjacent to the first wire portions 44 and 46 are spaced from each other along the select direction.

The second wire portion 50 of the first wire segment 101a is configured to extend toward the first wire portion 44 of the second wire segment 101b so as to at least partially define the second neck 42. Thus, the second wire portion 50 can be referred to as a second necked wire portion. For instance, the second wire portion 50 can extend toward the second wire portion 48 at the neck 42 substantially along a plane that includes the longitudinal direction L and the lateral direction A. Similarly, the second wire portion 48 of the second wire segment 101b is configured to extend toward the second wire portion 50 of the first wire segment 101a so as to at least partially define the second neck 42. Thus, the second wire portion 48 can be referred to as a second necked wire portion. For instance, the second wire portion 48 can extend toward the second wire portion 50 at the neck 42 substantially along a plane that includes the longitudinal direction L and the lateral direction A. The second wire portions 48 and 50 can be spaced from each other at the second neck 42, for instance along the lateral direction A, or the second wire portions 48 and 50 can abut each other at the second neck 42, for instance at a location that is coincident with the central axis AA. It should be appreciated, of course, that the second wire portions 48 and 50 can abut each other at any location with respect to the central axis AA, for instance offset from the central axis AA along the lateral direction A. Further, in embodiments wherein the second wire portions 48 and 50 are spaced from each other, the second wire portions 48 and 50 can be spaced from each other along a select direction, for instance the lateral direction A, a distance that is less than a distance that one or more adjacent portions of the respective wire segments 101a and 101b that are adjacent to the second wire portions 48 and 50 are spaced from each other along the select direction.

At least one or more of the first and second necks 40 and 42 can define abutment locations where the respective first wire portions 44 and 46, and second wire portions 48 and 50, abut each other. The first and second wire portions 44, 46, 48, and 50 of the implant body 15 may be stabilized relative to each other at the respective necks 40 and 42. For example, the stabilization may be provided through welding, soldering, gluing, or otherwise attaching the first wire portions 44 and 46 to each other, and through welding, soldering, or otherwise attaching the second wire portions 48 and 50 to each other, at the respective first and second necks 40 and 42. Thus, the respective first and second wire portions 44-50 can abut each other at the locations where they attach to each other, so as to secure the wire portions relative to each other, or can alternatively be attached to each other via an auxiliary attachment member that attaches to each of the respective wire portions, thereby securing the wire portions relative to each other. As the skilled person would of course understand other techniques or combination of techniques of attaching the wire segments 101a and 101b to each other at the necks 40 and 42 so as to stabilize the implant body 15 are of course possible. For example, the first wire portions 44 and 46 may be twisted about each other at the first neck 40 to provide the stabilizing feature, and the second wire portions 48 and 50 may be twisted about each other at the second neck 42 to provide the stabilizing feature. In another example, the twisted wire portions may be additionally spot welded, soldered, glued, or otherwise attached to each other to provide the stabilizing feature or features.

The bone implant 1 can define at least one or more, such as a plurality of, apertures, such as first and second apertures 30 and 32, respectively, that extend through the implant body 15 along the transverse direction. For instance, the first and second apertures 30 and 32 can be defined by the wire segments 101a and 101b. The first and second apertures 30 and 32 can be configured to receive a bone fixation element so as to secure the bone implant to the bone B, thereby stabilizing the first and second bone fragments FB and SB with respect to each other. Each of the first and second apertures 30 and 32 can be at least partially defined, at one or both of its longitudinal ends that are spaced from each other along the central axis AA, by one or two of the necks 40 and 42.

For instance, the first aperture 30 can be defined at a first longitudinal end, such as a distal longitudinal end, by the first neck 40, and can be defined at a second longitudinal end, such as a proximal longitudinal end, by a junction 21, which can be configured as a neck, that is connected between the first and second wire segments 101a and 101b at locations where the first and second wire segments 101a and 101b terminate. The junction 21 can an integral and monolithic junction between the first and second wire segments 101a and 101b, for instance when the segments 101a and 101b are part of the same wire 101, or can be a joint that attaches the first and second segments 101a and 101b to each other. For instance, the first wire segment 101a extends toward the junction 21 along the proximal direction, and the second wire segment 101b from the first wire segment 101a at the junction 21 along the distal direction. Alternatively, the first aperture 30 can be partially defined at its second longitudinal end by a neck as described above with respect to the first and second necks 40 and 42.

The second aperture 32 can be defined at a first longitudinal end, such as a distal longitudinal end, by the second neck 42, and can be defined at a second longitudinal end, such as a proximal longitudinal end, by the first neck 40. Thus, the first neck 40 can at least partially define both the first and second apertures 30 and 32. It should be appreciated that the first and second wire segments 101a and 101b can be constructed so as to not terminate at the respective first and second necks 40 and 42, but can rather extend beyond the first and second necks 40 and 42 in either or both of the proximal and distal directions. It should thus be appreciated that the junctions 21 can be connected between adjacent ones of the apertures of the bone implant 1, and can further connect the wire segments 101a-b, for instance at the proximal end 16 of the bone implant 16. One of the junctions 21 that connects the wire segments 101a-b at the proximal end 16 can further at least partially define one of the apertures, such as the aperture 30.

Each of the first apertures 30 can be defined at their respective first and second opposed lateral sides by the lateral side walls 38 and 36 that are spaced from each other along the lateral direction A, and thus also by the first and second wire segments 101a and 101b, respectively. For instance, the first lateral side wall 38 that extends continuously along the first lateral side of at least one or both of the first aperture 30 and the second aperture 32, between the respective necks that define the longitudinal ends of the first and second apertures 30 and 32, for instance from one of the respective necks to the other of the respective necks. The second lateral side wall 36 that extends continuously along the second lateral side of at least one or both of the first aperture 30 and the second apertures 32, between the respective necks that define the longitudinal ends of the first and second apertures 30 and 32, for instance from one of the respective necks to the other of the respective necks. For instance, each of the lateral side walls 38 and 36 can define a respective lateral inner surface 34 that faces the lateral inner surface 34 of the other of the lateral side walls 36 and 38, and defines the respective first lateral side and second lateral side, respectively, of at least one up to all of the apertures of the bone implant 1, including the first and second apertures 30 and 32.

Thus, the first and second lateral side walls 38 and 36, respectively, can extend along an entirety of at least one or both of the first and second apertures 30 and 32 so as to define the apertures 30 and 32 along with one or both of the necks 40 and 42 that are disposed at opposed ends of the respective apertures along the central axis AA. It should be appreciated that the first and second lateral side walls 38 and 36 are spaced from each other along the second direction, such as the lateral direction A, a first distance at a first one of the apertures. Further, the first and second lateral side walls 38 and 36 are spaced from each other along the second direction, such as the lateral direction A, a second distance at a second one of the apertures. The first and second side walls 38 and 36 can further extend continuously from a first end of the first aperture to a second end of the second aperture, such that the first and second ones of the apertures are disposed between the first and second ends. The first and second ends can define necks in the manner described above. The first and second side walls 38 and 36 can be spaced from each other along the second direction a third distance at the first end, and a fourth distance at the second end. Each of the third and fourth distances can be less than each of the first and second distances. The first and second distances can be different from each other or the same as each other. The third and fourth distances can be equal to each other or different than each other. The third and fourth distances can be substantially zero, for instance when the first and second side walls 38 and 36 abut each other.

The apertures of the bone implant 1, including the first aperture 30 and the second aperture 32 defined by the first and second wire segments 101a and 10ab, each extend along an insertion axis SA1 and SA2 that can extend between the bone-facing surface 19a and the opposed surface 19b. For instance, the insertion axes SA1 and SA2 can define central axes of the first and second apertures 30 and 32 that extend along the transverse direction T. Each of the apertures 30 and 32 can define a hole for receiving a bone fixation element therethrough along the respective insertion axis SA1 and SA1. The first and second wire segments 101 and 101b can lie in a plane that is defined by the longitudinal direction L and the lateral direction A, and is thus normal to the central axes of the first and second apertures 30 and 32. Accordingly, the bone contacting surface 19a may lie substantially flush to the bone B and the opposed outer surface 19b faces away from the bone contacting surface, and thus away from the bone B.

The aperture or plurality of apertures 30 and, 32 can be the same type of aperture (e.g., having the same size and shape), or can define different types of apertures (e.g., having a different one or both of size and shape). In accordance with the illustrated embodiment, the first aperture 30 can be of a first aperture type that is substantially circular, and the second aperture 32 can be of a second aperture type that is different from the first aperture type, and for instance can be elongate along the longitudinal direction L. Thus, reference herein to the reference numeral "30" and derivatives thereof can refer to the first aperture type, and reference herein to the reference numeral "32" and derivatives thereof can refer to the second aperture type. As the skilled person would understand any shaped aperture is of course possible. For example, either of the apertures may be polygonal. The inner surfaces 34 that define one or more up to all of the apertures, such as the first aperture 30, can be threaded. That is, the inner surfaces of the lateral side walls 36 and 38 can be threaded at locations where they define the first aperture 30, so as to define the threaded inner surface 34. The threaded inner surface 34 is configured to lockingly hold the bone fixation element in the bone implant 1. Accordingly, when the bone fixation element is driven into the bone B, the bone implant 1 secured to the bone B. In accordance with one embodiment, the threaded inner surface 34 is configured to threadedly engage complementary threaded head of a bone fixation element as described below with respect to FIG. 14B. Alternatively, the inner surface 34 can be unthreaded and substantially smooth so as to compress the bone implant 1 to the bone, as described below with respect to FIG. 14C. Alternatively still, the inner surface 34 can be unthreaded and substantially smooth, but shaped so as to threadedly mate with a threaded one fixation element, as described below with respect to FIG. 14A. Alternatively still, as described below with respect to FIG. 14D, the inner surface 34 can be threaded and configured to initially engage threads of the bone fixation element as the bone fixation element is inserted through the aperture, and then is configured to be received in a groove defined by the bone fixation element so as to secure the bone fixation element to the bone implant 1.

Alternatively or additionally, one or more of the apertures, such as the second aperture 32, is threadless and has a smooth inner surface. The aperture 32 may be used for compression of a bone fracture during an operation. For instance, as described in more detail below with respect to FIGS. 2F-G, a bone fixation element can be inserted through the aperture 32 and driven into a bone fragment, such that the bone fixation element can travel within the aperture 32 as the bone fragment is moved relative to another bone fragment. As the skilled person would understand, other types of hole may be provided. For example, the apertures may be a single type of a combination of types select from threaded, non-threaded, variable angle, compression and combi-hole. At least a portion of the second aperture 32 can alternatively define a threaded inner surface, such that the second aperture type can define a threaded inner surface or a smooth inner surface as desired.

With continuing reference to FIGS. 1A-C, the implant body 15, and in particular the wire segments 101a and 101b can be shaped to define a set of prongs 20. For instance, the first wire segment 101a defines a first prong 20a, and the second wire segment 101b defines a second prong 20b. In accordance with the illustrated embodiment, the first and second prongs 20a and 20b can define the distal terminal ends of the first and second wire segments 101a and 101b, respectively. The first wire segment 101a can extend along the inner transverse direction T with respect to a plane defined by the first and second wire segments 101a and 101b at each of the first and second apertures 30 and 32, so as to define the first prong 20a. The inner transverse direction T, and thus the outer transverse direction T, can include any direction that includes a directional component that extends along the transverse direction, and can further includes a directional component that is perpendicular to the transverse direction T. Similarly, the second wire segment 101b can extend along the inner transverse direction T, or at an angle offset from the inner transverse direction T, with respect to the plane defined by the first and second wire segments 101a and 101b at each of the first and second apertures 30 and 32, so as to define the first prong 20a. The first and second prongs 20a and 20b can extend parallel to each other, can diverge from each other along the inner transverse direction T, or can converge toward each other along the inner transverse direction T. The first and second wire segments 101a and 101b can further extend along the outer transverse direction T as they extend from one of the apertures 30 and 32, such as the second aperture 32, toward the respective first and second prongs 20a and 20b. Further, while the prongs 20 are illustrated as disposed at the distal end 17 of the bone implant 1, it should be appreciated that the prongs 20 can alternatively be disposed at the proximal end 16 of the bone implant 1.

The prongs 20 can be configured to be implanted into any suitable bone, such as the ulna, radius, tibia, fibula, and other similar bone, and for stabilizing a bone fragment, for example, the first bone fragment FB, which can be defined at the head of the bone B. In one embodiment, the prongs 20 can overlay the first bone fragment FB such that the first bone fragment is captured between the second bone fragment SB and the prongs 20. Thus, the prongs 20 can compress the first bone fragment FB against the second bone fragment SB, thereby maintaining reduction of the bone fracture. Alternatively, the prongs 20 can be configured to be driven into the bone, for instance the first bone fragment FB so as to stabilize the first bone fragment FB with respect to the second bone fragments SB. Further, the prongs 20 can be configured to receive a bone fixation element, such as a screw or a peg, that is configured to fix the prongs to the bone B. It should be appreciated that the prongs 20 and apertures 30 and 32 can define stabilization members that are configured to be secured to respective ones of the first and second bone fragments FB and SB of the bone B, either directly or via a bone fixation element, so as to secure the bone implant 1 to the first and second bone fragments FB and SB of the target bone B for supporting bone healing.

As illustrated in FIG. 1A, the bone implant 1 is shown implanted on the bone B. The prongs 20 are located in or on the first bone fragment FB and the remainder of the wire body 101 is positioned adjacent an outer surface of the bone B. The wire body 101 spans from the first bone fragment FB across the fracture location FL to the second bone fragment SB. Bone fixation elements can be subsequently inserted through at least one or more, up to all, of the apertures of the bone implant 1, such as the first and second apertures 30 and 32, along the respective insertion axes SA1 and SA2 so as to attach the bone implant 1 to the second bone fragment SB. Thus, the bone implant 1 can include a region disposed between the prongs 20 and at least one up to all of the apertures, including the first and second apertures 30 and 32, the region configured to overlie the fracture location FL. The prongs 20 can be attached to the first bone fragment FB in any manner as desired. For instance, the prongs 20 can be driven into the first bone fragment FB, or can capture the first bone fragment FB between the prongs 20, thereby stabilizing the first and second bone fragments FB and SB relative to each other. Further, the wire 101 can be flexible, such that the implant 1 can be resiliently extendable prior to fixation to one or both of the first and second bone fragments FB and SB. Accordingly, once the implant 1 has been fixed to the first and second bone fragments FB and SB, the implant 1 can apply a compressive force to the first and second bone fragments FB and SB so as to compress the first and second bone fragments FB and SB against each other at the fracture location FL. The wire 101 can be more resilient in contrast to a traditional bone plate which may increase micromovements between bone fragments thereby improving the quality of the bone generated during bone healing. It should be appreciated that the prongs 20a-b can define respective attachment locations of the bone implant 1, and that the attachment locations can alternatively be configured as apertures, as described below, or any suitable alternative structure that is configured to attach the bone implant 1 to bone.

Referring now to FIGS. 2A to 2D, the bone implant 1 can include any number of apertures that extend through the implant body 15 along the transverse direction T, and can define a respective third insertion axis SA3, as described above. For instance, the bone implant 1 can be as described above, and configured as a bone plate 2a constructed in accordance with an alternative embodiment. For instance, as described above, the bone implant 1 can include a third aperture 30' extend through the implant body 15, and can be located anywhere along the implant body 15. The third aperture 30' can be disposed between the second aperture 32 and the set of prongs 20. For instance, two or more up to all of the insertion axes SA1, SA2, and SA3 can be spaced equidistantly from each other along the distal direction, or can be spaced variably from each other. It should thus be appreciated that the bone plate 2a can have a length between the proximal and distal ends 16 and 17 greater than that of the bone plate 2.

Alternatively or additionally, the third aperture 30' can be disposed between the distal end 17 and the second aperture, and thus between the distal end 17 and the first aperture 30. Alternatively, the third aperture 30' can be disposed between the first aperture 30 and the second aperture 32. Alternatively or additionally, the third aperture 30' can be disposed between the proximal end 16 and the second aperture 32. The third aperture 30' can be positioned such that the region of the implant body 15 that is configured to overlay the fracture location FL (see FIG. 1A) can be disposed between the third aperture 30' and the set of prongs 20. Alternatively, the third aperture 30' can be positioned such that the region of the implant body 15 that is configured to overlay the fracture location FL can be disposed between the third aperture 30' and either or both of the first and second apertures 30 and 32.

The first and second wire segments 101a and 101b can define necks at opposed longitudinal ends of the third aperture 30', such that the first and second wire segments 101a and 101b extend beyond the respective necks of the third aperture 30' in either or both of the proximal and distal directions. Further, the neck that defines the proximal end of the third aperture 30' can also define the distal end of one of the first and second apertures 30 and 32, respectively. For instance, in accordance with the illustrated embodiment, the neck 42 can define both the proximal end of the third aperture 30' and the distal end of the second aperture 32.

Figure 2A:
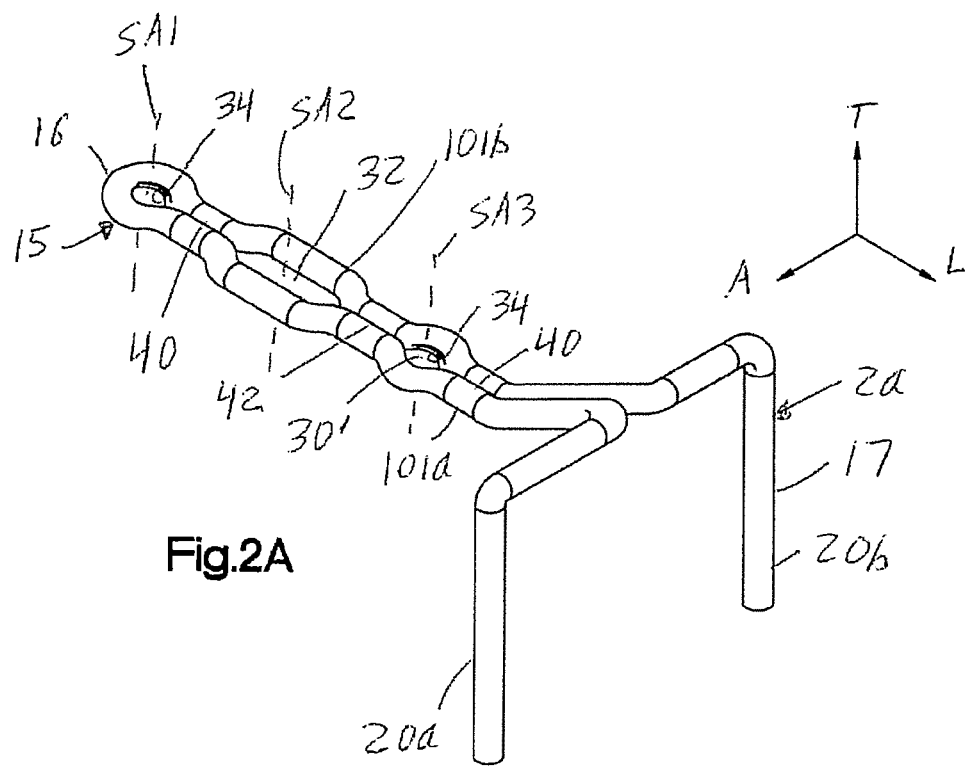
FIG. 2A is a perspective view of the bone implant as illustrated in FIG. 1A, but constructed in accordance with another embodiment.
Figure 2B:
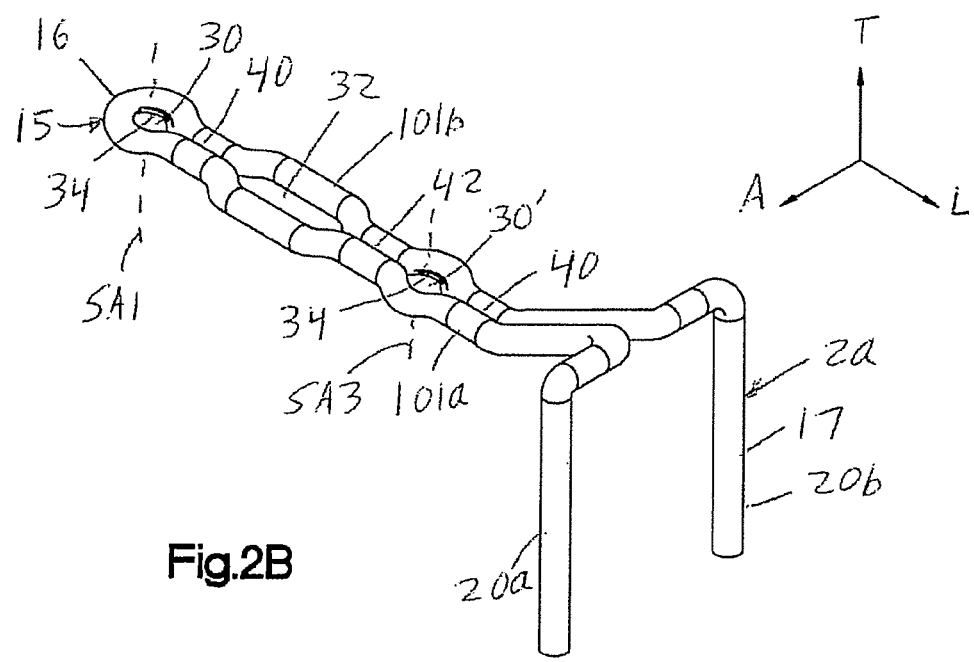
FIG. 2B is another perspective view of the bone implant illustrated in FIG. 2A.
Figure 2C:
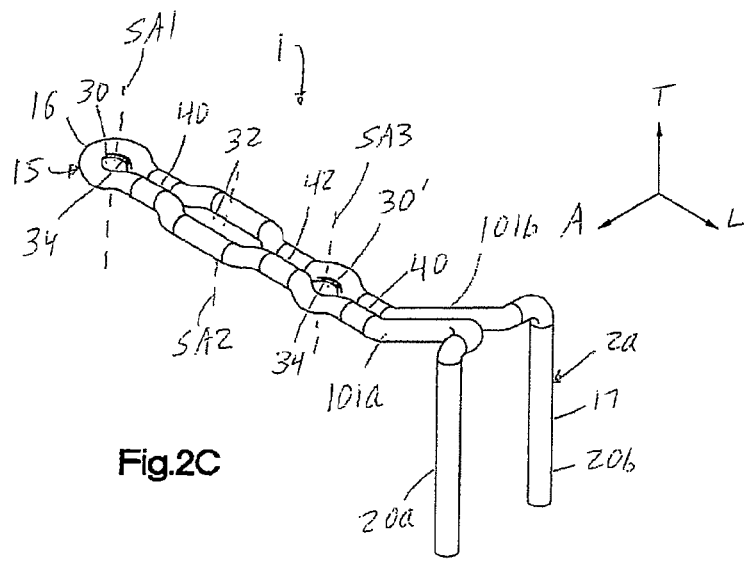
FIG. 2C is another perspective view of the bone implant illustrated in FIG. 2A.
Figure 2D:
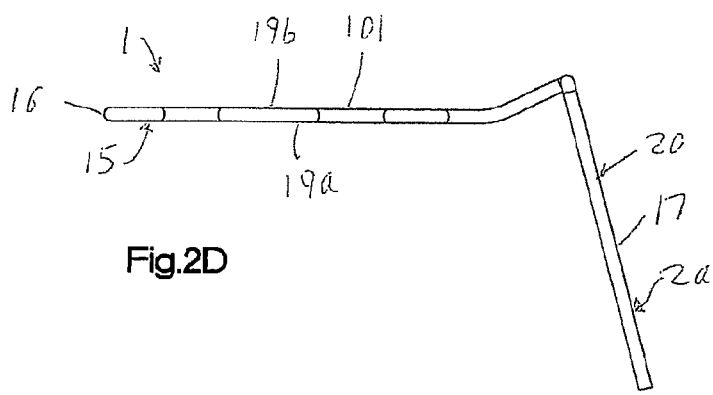
FIG. 2D is a side elevation view of the bone implant illustrated in FIG. 2A.
Figure 2E:
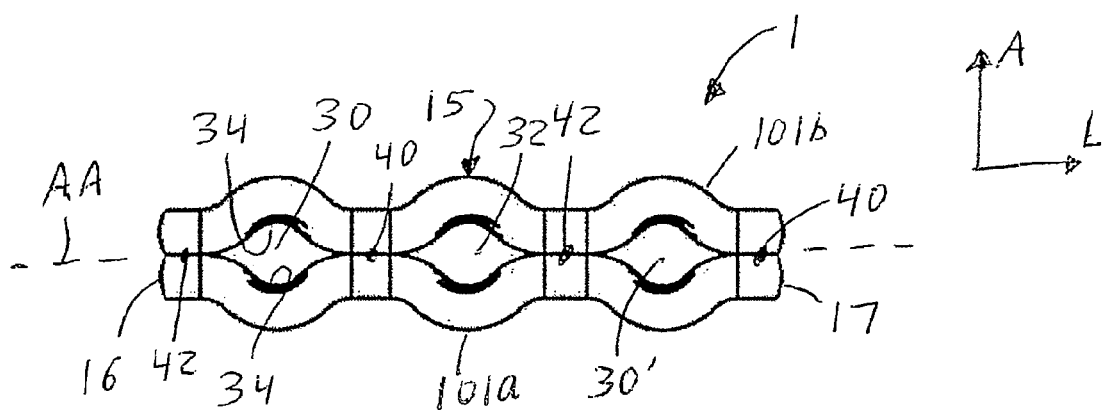
FIG. 2E is a top plan view of a bone implant constructed in accordance with another embodiment.

Referring to FIG. 2E, and as described above, any of the apertures 30 and 32 can define the first aperture type, and can thus be circular, or can define the second aperture type, and thus be elongate. For example, as illustrated in FIG. 2E, each of the first, second, and third apertures 30, 32, and 30', respectively, can define the first aperture type. The first and second wire segments 101a and 101b can define a plurality of first and second necks 40 and 42 on opposed ends of each of the apertures 30, 32, and 30' in the manner described above, and can attach to each other at the necks 40 and 42. Further, it should be further appreciated as described above that the first and second wire segments 101a and 101b can are separate from each other so as to define two separate wires 101 that are attached to each other so as to define the apertures 30, 32, and 30'. Thus, each of the proximal end distal ends 16 and 17 can define a respective one of the necks 40 and 42, whereby the first and second wire segments 101a and 101b are attached to each other. In accordance with one embodiment, all apertures of the bone implant 1 can be disposed between the necks 40 and 42 of the proximal end distal ends 16 and 17. Further, the neck 42 at the proximal end 16 can define one end of one of the apertures, such as the first aperture 30, and the neck 40 at the distal end 17 can define one end of one of the apertures, such as the third aperture 30'. The two wire segments 101a and 101b of this and any embodiment as described herein, unless otherwise indicated, can be mirror images of each other, for instance with respect to the central or longitudinal axis AA.

Figure 2F:
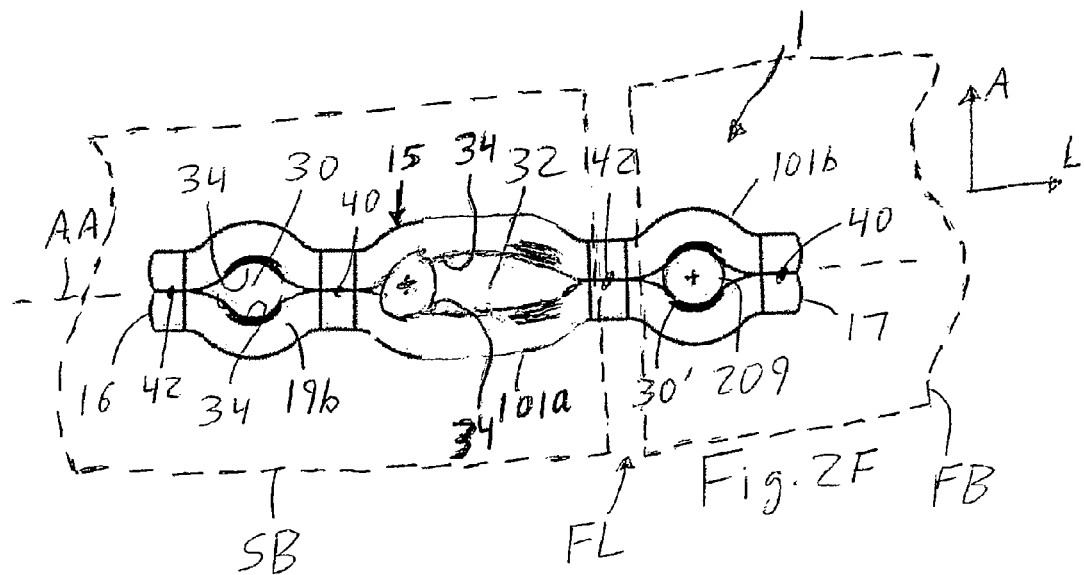
FIG. 2F is a top plan view of a bone implant system constructed in accordance with an embodiment, shown attached to a bone and configured to promote bone fracture reduction.
Figure 2G:
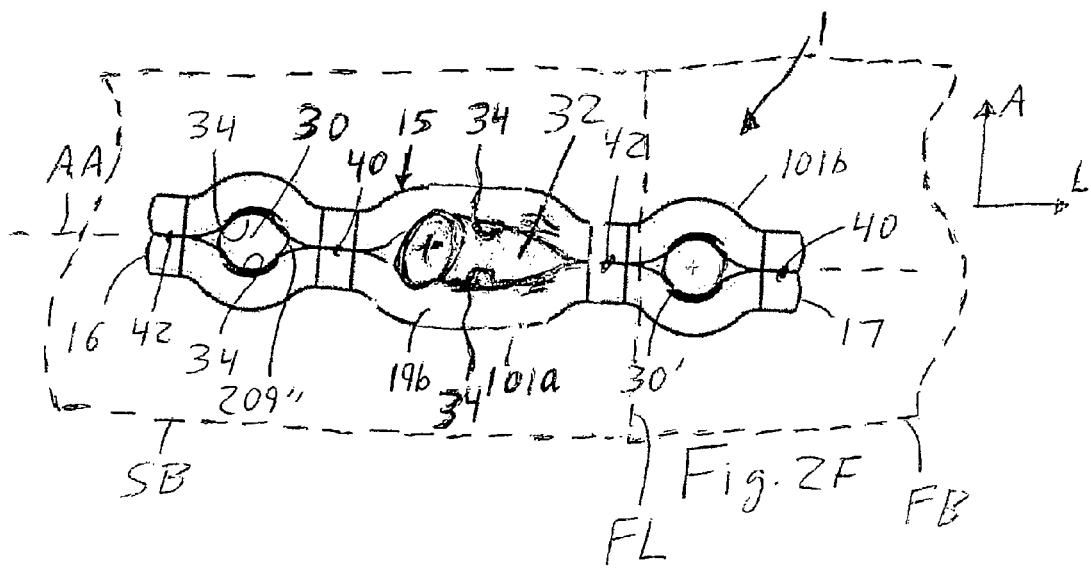
FIG. 2G is a top plan view of the bone implant system illustrated in FIG. 2F, shown after bone fracture reduction.

As described above with FIG. 2E, any of the apertures 30 and 32 can define the first aperture type, and can thus be circular, or can define the second aperture type, and thus be elongate. For example, referring to FIGS. 2F-2G, the second aperture 32 can be of the second aperture type, and can be elongate along the longitudinal axis AA. It is appreciated that the second aperture 32 can define a locking compression aperture configured to compress one or both of the first and second bone fragments FB and SB toward the other, so as to reduce the gap between the first and second bone fragments FB and SB at the fracture location FL. Furthermore, the second aperture 32 can be threaded such that a threaded bone fixation element can threadedly mate with the inner surface 34 in the second aperture 32. For instance, as illustrated in FIG. 2F, a first bone fixation element 209 can be inserted through the third aperture 30' and driven into a first one of the bone fragments. The third aperture 30' can be a threaded aperture, such that the first bone fixation element 209 is threadedly mated with the inner surface 34 at the third aperture 30' so as to attach the bone implant 1 to the first bone fragment FB. Alternatively, the first bone fixation element 209 can be sized to compress the bone implant body 15 against the first bone segment FB as it is driven into the first bone segment FB.

A second bone fixation element 209' can be inserted through the elongate aperture 32 and into the second bone segment SB at a first proximal end of the aperture 32 that is spaced from the distal end of the elongate aperture 32 along a proximal direction that is away the fracture location FL with respect to the proximal end. The proximal portion of the elongate aperture 32 can be unthreaded and the distal portion can be threaded and configured to mate with a threaded bone fixation element. The second bone fixation element 209' can be driven into the second bone segment SB such that the head of the second bone fixation element 209' rides along and cams over the curved inner wall 34 at the proximal end of the aperture 32, for instance at the opposed surface 19b, which causes the bone implant 1 to translate along the proximal direction. Because the third aperture 30 is secured to the first bone fragment FB that is spaced distal from the second bone fragment SB, the first bone fragment is urged to move toward the second bone fragment SB, thereby reducing the bone fracture at the fracture location. A third bone fixation element 209" can be driven into the first aperture 30, so as to secure the bone implant 1 to the second bone segment SB. For instance, the first aperture 30 can be threaded, and the third bone fixation element 209" can threadedly mate with the inner surface 34 at the first aperture, so that the bone implant is secured to the first and second bone fragments FB and SB when the bone fracture is reduced.

Figure 3A:
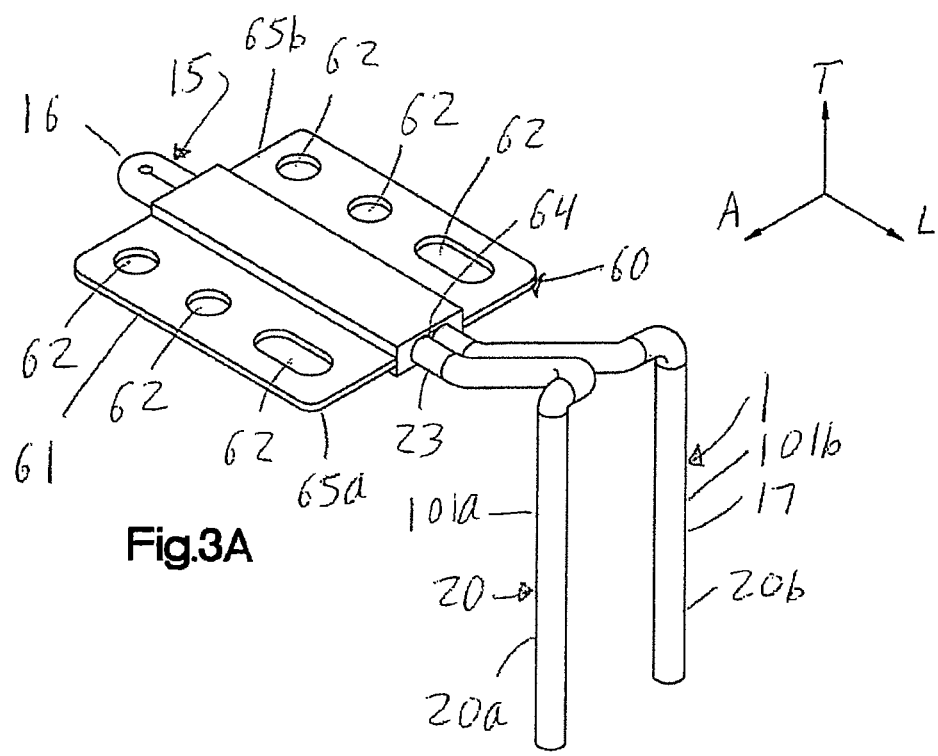
FIG. 3A shows a perspective view of a bone implant constructed in accordance with another embodiment.
Figure 3B:
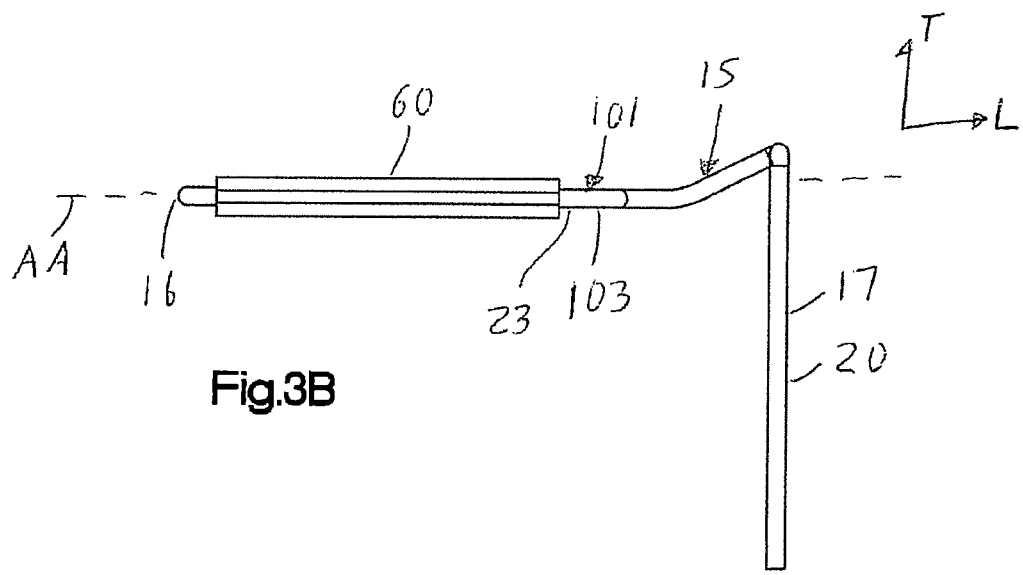
FIG. 3B is a side view of the bone implant illustrated in FIG. 3A.

Referring now to FIGS. 3A-B, the bone implant 1 can include a bone plate constructed in accordance with any embodiment described herein, unless otherwise indicated, in combination with an auxiliary bone fixation plate 60. At least a portion 23 up to all of the bone implant body 15 can be devoid of apertures, and can extend substantially linearly along the longitudinal direction L, and can be configured so as to be received in the auxiliary bone fixation plate 60. Alternatively, the auxiliary bone fixation plate 60 can be configured to attach to the bone implant 1, for instance in one of the apertures of the bone implant body 15. The portion 23 can be substantially linear, that is each of the first and second wire segments 101a and 101b can be substantially linearly elongate, for instance in the longitudinal direction L. The auxiliary bone fixation plate 60 can include a plate body 61 that defines a channel 64 configured to receive the portion 23 of the wire body. For instance, the channel 64 can be open at its inner transverse bone-facing end such that the channel 64 receives the portion 23 of the bone implant as the auxiliary bone fixation plate 60 is brought against the bone along the transverse direction T. Alternatively, the channel 64 can be enclosed at its inner transverse bone facing end, such that the channel 64 receives the first and second wire segments 101a and 101b as it travels with respect to the first and second wire segments 101a and 101b along the longitudinal direction L.

The auxiliary bone fixation plate 60 can include at least one or more plate sections, such as first and second plate portions 65a and 65b, respectively, that extend substantially laterally outward from the plate body 61. Thus, the plate body 61 can be disposed between the first and second plate portions 65a and 65b. The first and second plate portions 65a and 65b can be hingeable or otherwise flexible with respect to the plate body 61 so as to conform to the underlying bone. The auxiliary bone fixation plate can define one or more, up to a plurality of, apertures 62 that extend through either or both of the first and second plate portions 65a and 65b. The apertures 62 can be spaced along the longitudinal direction, and can be circular or elongate along the longitudinal direction, as described above with respect to the aperture 32. The apertures 62 are configured to receive respective bone fixation elements, such as bone screws, that fix to the underlying bone so as to capture the elongate portion 23 of the wire body 103 between the auxiliary bone fixation plate and the bone B, such as the first bone fragment FB or second bone segment, SB as described above.

Referring now to FIG. 4, a bone implant assembly 25 can include one or more of the bone implants 1 constructed in accordance with any embodiment described herein, or any alternative embodiments. The bone implant assembly 25 can include a first bone implant 1a configured as a first bone plate 2b, and a second bone implant 1b configured as a second bone plate 2c constructed in accordance with alternative embodiments. The bone plates 2b and 2c can be constructed substantially as described above with respect to the bone plates 2 and 2a, except the bone plates 2b and 2c are devoid of the prongs 20.

The first bone implant 1a can include an implant body 15a constructed as described above with respect to the implant body 15. Thus, the implant body 15a can include a first wire segment 101a and a second wire segment 101b as described above. The implant body 15a can further include a third wire segment 101c that can be integral and monolithic with the first and second wire segments 101a and 101b, or can be separate from and attached to one or both of the first and second wire segments 101a and 101b along the first and second necks 40 and 42, and any additional necks of the bone implant 1a as desired. For instance, the necks 40 and 42 can be defined at locations where one or both of the wire segments 101a and 101b extends toward the other of the wire segments 101a and 101b, for instance where the first and second wire segments 101a and 101b contact each other, and where one of the second and third wire segments 101b and 101c extends toward the other, for instance contacts, of the second and third wire segments 101b and 101c. The third wire segment 101c can be welded, soldered, or otherwise attached to the second wire segment 101b at the locations where the third wire segment 101c contacts the second wire segment 101b. The first bone implant 1a can include the auxiliary bone fixation plate 60 in the manner described above.

Furthermore, the distal ends of one or more, up to all, of the wire segments 101a-c can diverge with respect to one or more, up to all, of the other of the wire segments 101a-c as they extend along the distal direction. Thus, the wire segments 101a-c can define respective tines 27a-c at the distal end 17 of the implant body 15a. The implant body 15a can further define at least one or more apertures 30 that extend through the tines 27a-c, for instance at the distal end of the tines 27a-c. The apertures 30 are configured to receive respective bone fixation elements, such as bone screws, that fix to the underlying bone so as to fix the wire segments 101a-c to the bone B, such as the first bone fragment FB or second bone segment, SB as described above. The apertures 30 can be constructed as the first aperture type described above, and can be defined by bending the wire segments 101a-101c about themselves. For instance, the distal ends of each of the wire segments 101a-101c can extend distally, and can be bent along a circular path so as to extend proximally and thus define the apertures 30.

With continuing reference to FIG. 4, the second bone implant 1b can be constructed substantially as described with respect to the first bone implant 1a, except the implant body 15b of the second bone implant 1b includes the first and second wire segments 101a and 101b as described above, but not the third wire segment 101c. Thus, the distal ends of one or both of the wire segments 101a-b can diverge with respect to the other they extend along the distal direction. Accordingly, the first and second wire segments 101a-b can define respective tines 27a-b at the distal end 17 of the implant body 15a. The implant body 15a can further define at least one or more apertures 30 that extend through the tines 27a-b, for instance at the distal end of the tines 27a-b. The apertures 30 are configured to receive respective bone fixation elements, such as bone screws, that fix to the underlying bone so as to fix the wire segments 101a-c to the bone B, such as the first bone fragment FB or second bone segment, SB as described above. The apertures 30 can be constructed as the first aperture type described above, and can be defined by bending the wire segments 101a-101b about themselves. For instance, the distal ends of each of the wire segments 101a-101b can extend distally, and can be bent along a circular path so as to extend proximally and thus define the apertures 30.

Figure 5A:
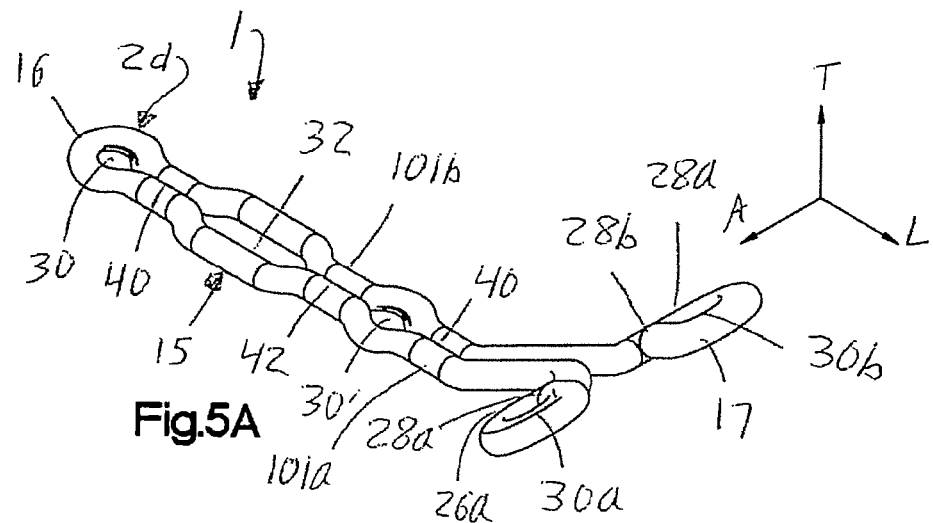
FIG. 5A is a perspective view of a bone implant constructed in accordance with another embodiment.
Figure 5B:
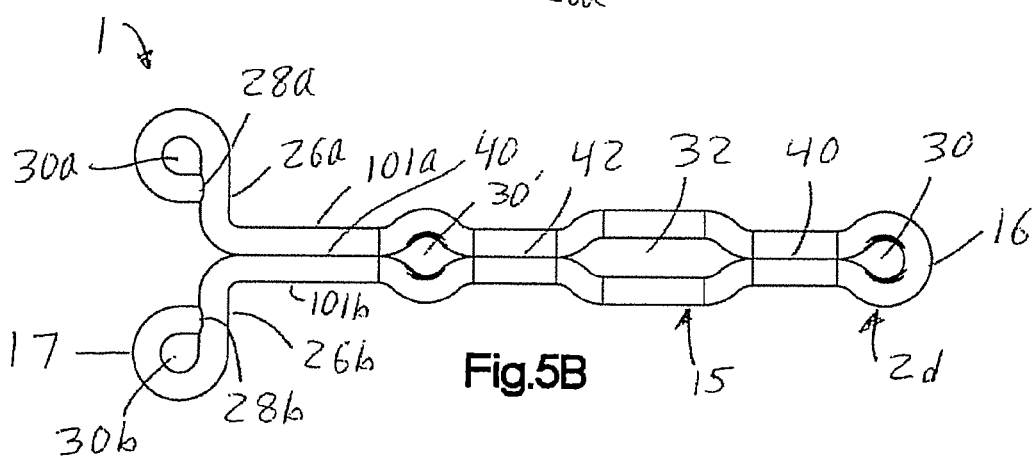
FIG. 5B is a plan view of the bone implant illustrated in FIG. 5A.
Figure 5C:
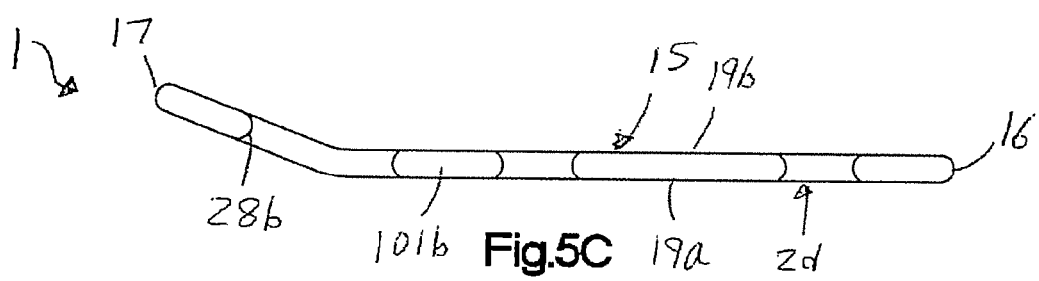
FIG. 5C is a side elevation view of the bone implant illustrated in FIG. 5A.

Referring now to FIGS. 5A-5C, the bone implant 1 can be constructed as a bone plate 2d that can be constructed substantially as described above with respect to the bone plate 2a, with the exception that the implant body 15, and in particular the first and second wire segments 101a and 101b, respectively, define corresponding first and second apertures 30a-b, respectively, in place of the prongs 20a-b of the bone plate 2a. The apertures 30a-b can be constructed as the first aperture type as illustrated, though it should be appreciated that the apertures 30a-b can alternatively be constructed as the second aperture type as desired. Each of the apertures 30a and 30b can be formed by bending each of the wire segments 101a-b around themselves. For instance, the wire segments 101a and 101b can define a neck 40 disposed distal of the third aperture 30', and that can define the distal end of the third aperture 30' as described above. The tines 20 described above can extend from the neck 40, or the apertures 30a-b can extend from the neck 40. For instance, each of the wire segments 101a and 101b, and thus the implant body 15, can define a respective base 26a and 26b. The bases 26a and 26b can be angularly offset from the neck 40, or can be inline with the neck 40 as desired. In accordance with the illustrated embodiment, the bases 26a and 26b are elongate along a direction that extends outward along the lateral direction A, for instance perpendicular, from the neck 40. Thus, the bases 26a and 26b can extend from the neck 40 in opposite directions. The first and second wire segments 101a and 101b are bent around a path, such as a circular path, so as to define respective first and second terminal ends 28a and 28b that are disposed at adjacent the respective bases 26a and 26b. Thus, it can be said that the implant body 15 defines the first and second terminal ends 28a and 28b, respectively. The terminal ends 28a and 28b can abut the respective bases 26a and 26b, and can be welded, soldered, or otherwise attached to the respective bases 26a and 26b as desired. In one embodiment, the terminal ends 28a and 28b are not fixed to their respective bases 26a and 26b.

In accordance with the illustrated embodiment, and all other embodiments unless otherwise indicated, the wire segments 101a and 101b can be bent so as to orient the respective apertures 30 and 32, and derivatives thereof, in alignment with the underlying bone. For instance, the bases 26a and 26b can be bent or otherwise shaped as desired such that the respective apertures 30a and 30b are aligned with the underlying bone B, and the portion of the respective wire segments 101a and 101b that defines the respective apertures 30a and 30b conform to the underlying bone. It should thus be further appreciated that the wire segments 101a and 101b can be bent or otherwise shaped such that the apertures 30, 30', and 32 are aligned with the underlying bone, and the portions of the respective wire segments 101a and 101b that define the respective apertures 30, 30', and 32 conform to the underlying bone.

Figure 6:
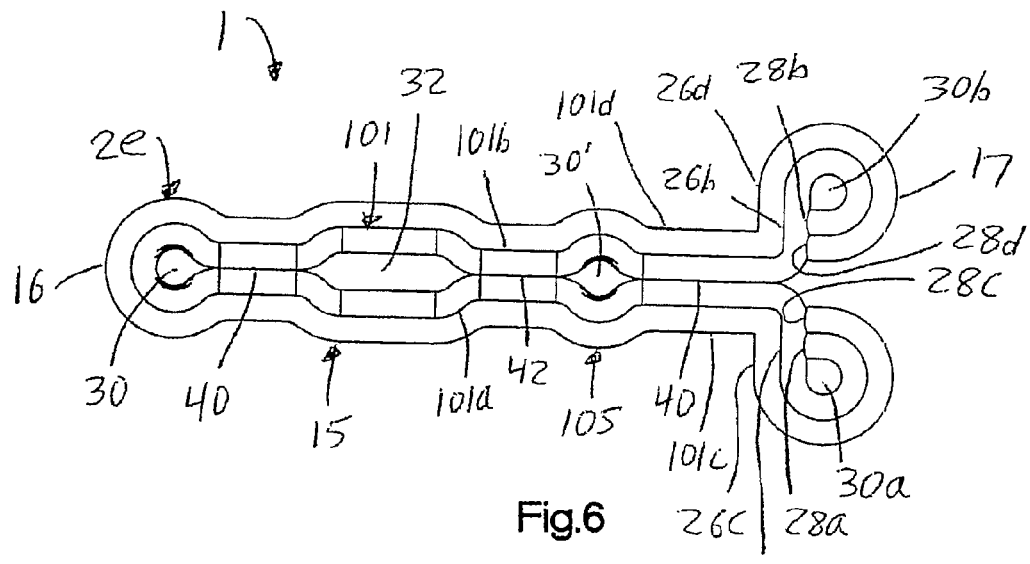
FIG. 6 is a plan view of a bone implant constructed in accordance with another embodiment.

Referring now to FIG. 6, the bone implant 1 can be configured as a bone plate 2e that is constructed substantially as described above with respect to the bone plate 2d of FIGS. 5A-C, with the exception that the bone plate 2e, and thus the bone implant body 15, and thus the bone implant 1, can include third and fourth wire segments 101c and 101d, respectively. The third and fourth wire segments 101c and 101d that can be constructed substantially as described above with respect to the first and second wire segments 101a and 101b. For instance, the wire 101 of the implant body 15 can define a first wire, and the implant body 15 can include a second wire 105 that defines the third wire segment 101c and the fourth wire segment 101d. It should be appreciated that the third and fourth wire segments 101c and 101d can be integral and monolithic with each other, such that they form part of the second wire 105. Alternatively, the first and third and fourth wire segments 101c and 101d can be separate from each other, and defined by two different respective wires. One or both of the third and fourth wire segments 101c and 101d can further be integral and monolithic with the wire 101, or can be separate from, and attached to, the wire 101.

The second wire 105, and thus either or both of the third and fourth wire segments 101c and 101d, can extend about the outer lateral perimeter of at least a portion up to all of each of the first and second wire segments 101a and 101b. The third and fourth wire segments 101c and 101d can further be attached to, for instance welded, soldered, or otherwise attached to the first and second wire segments 101a and 101b along at least a portion up to all of the length of the third and fourth wire segments 101c and 101d. Thus, the third and fourth wire segments can define respective bases 26c and 26d that are configured as described above with respect to the first and second bases 26a and 26b, and can be bent from the respective bases 26c and 26d along a path, such as a circular path, so as to define respective terminal ends 28c and 28d that are disposed at adjacent the respective bases 26a and 26b of the first and second wire segments 101a and 101b. Thus, it can be said that the implant body 15 defines the third and fourth terminal ends 28c and 28d, respectively, along with the third and fourth bases 26c and 26d. The terminal ends 28c and 28d can abut the respective bases 26a and 26b, and can be welded, soldered, or otherwise attached to the respective bases 26a and 26b as desired. In one embodiment, the terminal ends 28c and 28d are not fixed to their respective bases 26a and 26b.

As the skilled person would understand any number of wires may be bent around and fixed to adjacent wires. The additional wires may be provided to increase the rigidity of the bone implant 1. It should be appreciated that the additional wires, including the second additional wire 105, can be attached to the first wire 106 only at regions disposed proximate to, for instance surrounding, the apertures 30, 30', 32, 30a, and 30b as well as the necks 40 and 42 so as to provide structural rigidity to the bone implant 1 at the apertures. Thus, the second wire 105 and the additional wires can be segmented and discontinuous along the first and second wire segments 101a and 101b, or can be continuous along the first and second wire segments 101a and 101b.

Figure 7A:
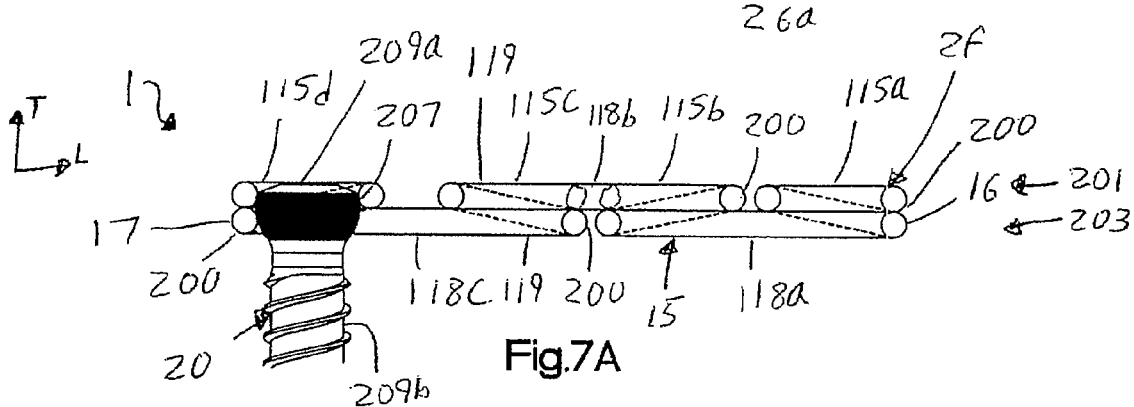
FIG. 7A is a sectional side elevation view of a bone implant constructed in accordance with another embodiment.
Figure 7B:
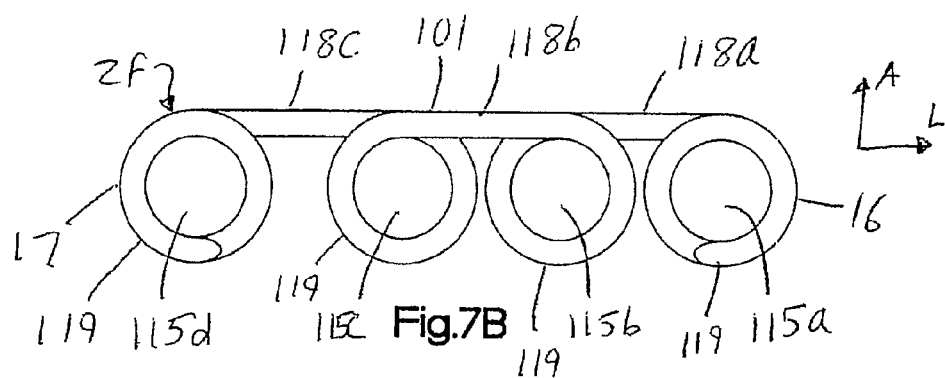
FIG. 7B is a plan view of the bone implant illustrated in FIG. 7A, rotated 180°.

Referring now to FIGS. 7A-B, the bone implant 1 can be configured as a bone plate 2f constructed in accordance with an alternative embodiment. The bone plate 2f, and thus the bone implant 1, can include the wire 101 that defines the implant body 15 in the manner described above. The wire 101, and thus the implant body 15, can define at least one or more, such as a plurality of, bone fixation element apertures, such as first, second, third, and fourth apertures 115a, 115b, 115c, and 115d respectively. The apertures 115a-115d can be configured as the first aperture type as described above, and can alternatively be configured as the second aperture type. The apertures 115a-d can be aligned with the underlying bone when the bone implant is positioned to be attached to the underlying bone in the manner described above. In accordance with one embodiment, the wire 101 can be spiraled about itself, for instance along a substantially circular, elongate, or alternatively shaped path, in at least one, such as a plurality, of respective successive loops 119 so as to define the apertures 115a-115d. As can be seen in FIG. 7A a first spiral 200 can be formed for each of the apertures 115a-115d, but as the skilled person would understand any number of spirals can be formed. The wire 101 can thus extend continuously from a first end of each of the apertures 115a-115d to a second of each of the apertures that is spaced from the first end of each of the apertures 115a-d along the central axis of the bone implant 1, can define first and second lateral side walls that define each of the apertures 151a-d.

The spirals 200 can define a first layer 201 and a second layer 203 of wire 101 that is spaced from the first layer 201 along the inner transverse direction T. For instance, the second layer 203 can abut the first layer 201. One or more of the spirals 200 can be attached (e.g., welded, glued, or the like) to another of the spirals 200, for instance at an interface between the first layer 201 and the second layer 203. As can be seen, the spiral 200 of the wire 101 that defines a first proximal-most one 115a of the apertures can begin at the first layer 201 so as to define a first loop 119 at the first layer 201, and can then extend from the first layer 201 to the second layer 203 and define a second loop 119 at the second layer 203. The wire 101 can then extend along the second layer 203, for instance in the distal direction, so as to define a first junction 118a between the first aperture 115a and the second aperture 115b.

The wire 101 can then define another spiral 200 at the second layer 203 so as to define a first loop 119 of a second aperture 115b that is disposed distal of the loops 119 of the first aperture 115a. The wire 101 spirals to the first layer 201 to form the second loop 119 of the second aperture 115b that is spaced from the first loop 119 of the second aperture along the outer transverse direction. The wire 101 can then extend along the first layer 201, for instance in the distal direction, so as to define a second junction 118b between the second aperture 115b and the third aperture 115c.

The wire 101 can then define another spiral 200 at the first layer 201 so as to define a first loop 119 of the third aperture 115c that is disposed distal of the loops 119 of the second aperture 115b. The wire 101 spirals from the first layer 201 to the second layer 203 to form a second loop 119 of the third aperture 115c that is spaced from the first loop 119a of the third aperture 115c along the inner transverse direction. The wire 101 can then extend along the second layer 203, for instance in the distal direction, so as to define a third junction 118c between the third aperture 115c and the fourth aperture 115d.

The wire 101 can then define another spiral 200 at the second layer 203 so as to define a first loop 119 of the fourth aperture 115d that is disposed distal of the loops 119 of the third aperture 115c. The wire 101 spirals from the second layer 203 to the first layer 201 to form a second loop 119 of the fourth aperture 115d that is spaced from the first loop 119a of the fourth aperture 115d along the outer transverse direction. The wire 101 can then terminate at the first layer 201, or can continue so as to define one or more successive spirals 200 and corresponding loops 119, and thus apertures, in the manner described above.

It should thus be appreciated that the wire 101 can spiral from one of the first and second layers 201 and 203 to the other of the first and second layers 201 and 203 to form any of the apertures as desired, connected to each other by a junction, and the corresponding shape of the bone implant as desired. The wire 101 can be attached to itself, for instance welded, soldered, or the like, at various locations around the loops 119, for instance between the successive first and second loops 119 of the first layer and second layers 201 and 203, so as to define a stable structure that surrounds and defines the apertures 115a-d. The spirals 200 of one or more up to all of the apertures 115a-d can define at least one thread, in which a bone fixation element 209 having a head 209a and a shaft 209b that extends out from the head 209a, and a convex groove 207 formed in the head 209a. The groove 207 can be adapted to the diameter of the wire 101 that forms the bone plate 2f. For instance, the groove 207 can be defined by a radius that is the same as the radius that defines the wire 101, such that the groove 207 can threadedly engage the wire 101. Thus, the wire 101 can be shaped so as to define a threaded aperture configured to mate with complementary threads of the head of a bone fixation element.

The spirals 200 can define any number of loops 119 and respective layers, and any number of corresponding threads, as desired. The spirals 200 forming the apertures 115a-d can have the same diameter chosen according to the fixation element 209 to be inserted therethrough. For example, the shaft 209b, which can be a screw shaft, may have a diameter of 1.5 mm to 3.0 mm, and the head 209a can define any cross-sectional dimension, such as a diameter, as desired, for instance of 2.0 mm to 4.5 mm. It should be appreciated that any of the bone plates described herein can include at least one of the apertures 115 unless otherwise indicated.

Referring now to FIG. 8, the bone implant 1 can be configured as a bone plate 2g constructed in accordance with an alternative embodiment that can be configured to be implanted on the underlying bone, where the underlying bone is a patella. As described above, the implant 1 can define any size and shape as desired. For instance, the implant 1 can include a plurality of implant bodies 15, such as six implant bodies 15 or any number of implant bodies 15, as desired, that are attached to a common central point or hub 217. The plurality of implant bodies 15 can be integral and monolithic with each other. The plurality of implant bodies 15 can define respective fingers 215 that extend radially outward from the hub 217, such that the bone implant 1 is substantially star-shaped. Each of the plurality of implant bodies 15 can be integral and monolithic with each other and the hub 217, or can be separate from each other and the hub 217 and attached to each other and the hub 217, in any manner as desired. Each implant body 15 can include a first wire segment 101a and a second wire segment 101b that define necks 40 and 42, and apertures 30 and 30' constructed in the manner described above, for instance, with respect to FIGS. 1A-C. One or more of the apertures 30 and 30' can be configured as the first aperture type, or can be constructed as the second aperture type (for instance as described above with respect to the apertures 32) as desired. Alternatively or additionally, one or more of the apertures 30 can be constructed as described above with respect to the apertures 115a-d (see FIGS. 7A-B). Alternatively or additionally still, one or more of the apertures 30 can be defined by the wire segments 101a-b in the manner described above, or may be punched through the wire segments 101a-b. In this regard, any bone fixation element receiving aperture of any bone implant 1 described herein, or alternatives thereof, can be constructed as described above with respect to the aperture 30, the aperture 32, the aperture 30', the aperture 30a, the aperture 30b, and the apertures 115a-d, unless otherwise indicated. The implant bodies 15 can define any number of bone apertures as desired. For instance one of the implant bodies 15 can define three apertures 30 while the other implant bodies 15 can define two apertures 30. It should be appreciated of course that each of the implant bodies 15, and thus the bone implant 1, can define any number of apertures 30 as desired. Each implant body 15 can have the same number or a different number of apertures 30 as one or more up to all of the other fingers 215.

The first and second wire segments 101a and 101b disposed at the distal end 17 of each implant body 15 can each define a junction 218 that extends to the distal end 17 of an adjacent one of the implant bodies 15. The wire segments 101a and 101b can then extend proximally from the respective junctions 218 so as to define the implant body 15. Thus, the hub 217 can be defined by the junctions 218 that connect each of the implant bodies 15 to each other, for instance at their distal ends 17. In one embodiment, each implant body 15 can extend from the hub 217 the same angle or a different angle relative to its neighboring implant body 15, it being appreciated that the implant 1 can be flexible so as to reposition one or more of the implant bodies 15 toward or away from one or its neighboring implant bodies 15, thereby adjusting the angle formed between the wire segments 101a and 101b at the distal end 17 and the respective junctions 218. In accordance with another embodiment, it is envisioned that the underlying patella may have a particular fracture pattern and the fingers can be adapted according to the fracture pattern. The implant 1 can include any number of implant bodies 15 as desired.

Referring now to FIG. 9, the bone implant 1 can include a bone plate 2h constructed in accordance with another embodiment, and can include a plurality of implant bodies 15 that each include first and second wire segments 101a and 101b in the manner described above. The wire segments 101a and 101b of each of the implant bodies 15 can be separate from the wire segments 101a and 101b of the other implant bodies 15. Further, the first and second wire segments 101a and 101b of each implant body can be integral and monolithic with each other and can thus be formed from a single wire 101, or can be separate from each other and attached to each other. Thus, the wires 101 that define the first and second wire segments 101a-b of each implant body 15 can be separate from another, and attached to at least one or more of the other wires 101 of the other implant bodies 15 of the bone implant 1. The bone implant 1 can thus include a plurality of the implant bodies 15 that are separate from each other and attached to at least one or more others of the implant bodies 15.

The implant bodies 15 can be configured in accordance with any embodiment described herein. Thus, the implant bodies 15 can include the first and second wire segments 101a and 101b that defines junctions, which can be necks 40 and 42, that at least partially define apertures that extend through the implant body 15, including the apertures 30. One or more up to all of the apertures 30 can be constructed as the first aperture type as described above, or can be constructed as the second aperture type as described above. One or more of the implant bodies 15 can define any number of apertures 30 as desired, including a greater number of apertures 30 than the number of apertures 30 of one or more up to all of the other implant bodies 15, or a lesser number of apertures 30 than the number of apertures 30 of one or more up to all of the implant bodies 15. One or more of the apertures 30 can be configured as the first aperture type, or can be constructed as the second aperture type (for instance as described above with respect to the apertures 32) as desired. Alternatively still, one or more of the apertures 30 can be constructed as described above with respect to the apertures 115a-d (see FIGS. 7A-B).

The discrete implant bodies 15 can be attached to from the bone plate 2h according to a predetermined shape of a target bone to which the bone implant 1 is to be attached. For instance, the bone plate 2h can be configured to attach to an underlying volar column of a distal radius. For instance, a first implant body 15a of the implant bodies 15 can be configured to attach to the diaphysis of the distal radius, while one or more second implant bodies 15b of the implant bodies 15 are configured to attach to the metaphysis alone or in combination with the epiphysis of the distal radius. The bone plate 10 shown includes four implant bodies 15, and thus four respective wires 101. In accordance with the illustrated embodiment, select ones of the implant bodies 15 can include two, three and four apertures 30, respectively. However, it should be appreciated that the implant bodies 15 can include a fewer or a greater number of apertures 30 as desired. When the bone implant 1 is attached to the underlying bone, the apertures 30 of the second implant bodies 15b can be aligned with the metaphysis or the epiphysis, and the apertures 30 of the first implant body 15a can be aligned with the diaphysis. Accordingly, when bone fixation elements are inserted through the apertures 30 of the second implant bodies 15b, the bone fixation elements are driven into the metaphysis or the epiphysis. When the bone fixation elements are inserted through the apertures 30 of the first implant bodies 15a, the bone fixation elements are driven into the diaphysis. Thus, the fracture location of an underlying bone can be disposed between at least one or more, up to all of, the apertures 30 of the first implant body 15a and at least one aperture of one or more, up to all, of the second implant bodies 15b.

The implant bodies 15, and thus the first and second wire segments 101a-b, can define male undulations 121a, defined by convex regions of the outer periphery of the respective implant body 15, and female undulations 121b, defined by concave regions of the outer periphery of the respective implant body 15. Thus, at least one or both of the wire segments 101a and 101b can define the male undulations 121a and the female undulations 121b that alternate with each other along at least a portion of the length of the respective implant body 15. For instance, the female undulations can be defined by the necks 40 and 42, and the male undulations can be defined at the proximal end 16, the distal end 17, which can define an aperture 30 as described above with respect to the aperture 30 at the proximal end 16 illustrated in FIGS. 1A-C. The male undulations 121a can further be defined at regions of the wire segments 101a-b that define the apertures 30. It should be appreciated that the male undulations 121a of one of the implant bodies 15 can be configured to nest in the female undulations 121b of another of the implant bodies 15. Otherwise stated, the female undulations 121b of one of the implant bodies 15 can be configured to receive the male undulations 121a of another of the implant bodies 15. The male and female undulations 121a and 121b can be welded, glued, bonded, soldered, pressed, twisted, clamped, or otherwise attached to each other in any manner as desired. Alternatively, the male undulations 121a can abut each other and be welded, glued, bonded, soldered, pressed, twisted, clamped, or otherwise attached to each other in any manner as desired.

For instance, the male undulation 121*a* defined by the distal end 17 of the first implant body 15*a* can be received by a first female undulation 121*b* disposed between a pair of apertures 30 of a proximal-most one of the second implant bodies 15*b*. Thus, the central axis AA of the first implant body 15*a* is angularly offset, for instance substantially perpendicular, with respect to the central axis AA of the implant body 15 to which the first implant body is attached. The central axes AA of the second implant bodies 15*b* that are attached to each other at their respective male and female undulations 121*a* and 121*b* can extend substantially parallel to each other. The first and second wire segments 101*a* and 101*b* of each of the implant bodies 15 can define male and female undulations, and at least one of the male undulations of one of the implant bodies is received in at least one of the female undulations of another one of the implant bodies, and attached to the another one of the implant bodies at an interface between the at least one of the male undulation and the at least one of the female undulations.

Referring now to FIG. 10, the bone implant 1 can include a bone plate 2*i* constructed in accordance with another embodiment, and can include a plurality of implant bodies 15 that each include first and second wire segments 101*a* and 101*b* in the manner described above. The bone plate 2*i*, and thus the bone implant 1, can be constructed substantially as described above with respect to the bone plate 2*h* of the bone implant 1 in FIG. 9 in that the bone implant 1 includes a plurality of discrete implant bodies 15 attached together to define the bone plate 2*i*. The bone implant 1 can include a plurality of first implant bodies 15*a* that are arranged such that their male undulations 121*a* abut each other, and are attached to each other. For instance, the plurality of first implant bodies 15*a* can include a first implant body 15*a*1 that can define a proximal implant body, a second implant body 15*a*2, that can define a middle implant body, and a third implant body 15*a*3 that can define a distal implant body, such that the second implant body 15*a*2 is disposed between the first and third implant bodies 15*a*1 and 15*a*3. The central axes 15*a*1-15*a*3 can be substantially coincident with each other. The distal end 17 of the first implant body 15*a*1 can abut and attach to the proximal end 16 of the second implant body 15*a*2, for instance at the respective male undulations 121*a*, in any manner as described herein. The distal end 17 of the second implant body 15*a*2 can be attached to the proximal end 16 of the third implant body 15*a*3, for instance at the respective male undulations 121*a*, in any manner as described herein.

Further, at the second implant bodies 15*b* can include a first implant body 15*b*1 and a second implant body 15*b*2 that is attached to the first implant body 15*b*1 and respective ends, such as the proximal ends 16, in accordance with any embodiment described herein. The first and second implant bodies 15*b*1 and 15*b*2 can extend oblique to each other such that the respective male undulations 121*a* at the attached ends can combine to define a female undulation 121*b*. The male undulation 121*a* of one of the first implant bodies 15*a*, such as the third one 15*a*3 of the first implant bodies 15*a*, which can be disposed at the proximal end 16, can be received in the female undulation 121*b* that is defined by the first and second implant bodies 15*b*1 and 15*b*2. Accordingly, it should be appreciated that one or more up to all of the female undulations 121*b* of the bone implant 1 can be defined by a single implant body 15 or a pair of implant bodies 15. Thus, it can be said that one or more up to all of the female undulations 121*b* can be defined by at least one implant body 15.

The second implant bodies 15*b* can include a third implant body 15*b*3 and a fourth implant body 15*b*4 that are attached to the first implant body 15*b*1 and the second implant body 15*b*2, respectively. For instance, the female undulations 121*b* of the third and fourth implant bodies 15*b*3 and 15*b*4 can receive the male undulations 121*a* of the first and second implant bodies 15*b*1 and 15*b*2 that are disposed at one end, such as the distal end, of the first and second implant bodies 15*b*1 and 15*b*2. Thus, the central axes of the third and fourth implant bodies 15*b*3 and 15*b*4 can be substantially aligned with each other, oblique to the central axes of the first and second implant bodies 15*b*1 and 15*b*2, and substantially perpendicular with respect to the first implant bodies 15*a*.

As described above, the apertures of the bone implant 1 that extend through the bone implant bodies 15 can be of any size and shape. For instance, one or more up to all of the apertures 30 can define a compression aperture 223 that decreases the length of the bone implant 1 along the central axis AA of the bone implant 1. While one of the apertures 30, which is constructed as the first aperture type as described above, can define the compression aperture 223, it should be appreciated that any apertures described herein can define a compression feature in the manner described below, unless otherwise indicated. It should further be appreciated that the compression aperture 223 can be configured to receive a bone fixation element that attaches to the underlying bone, or can be configured not to receive a bone fixation element that attaches to the underlying bone and whose sole function is to decrease the length of the bone implant 1 from the proximal end to the distal end of the bone implant 1 along the central axis AA of the bone implant 1.

The portions of the first and second wire segments 101*a* and 101*b* that define the compression aperture 223, for instance at their lateral side walls 38 and 36, respectively, can be crimped in a select direction, such as the in the longitudinal direction L or in a direction that is angularly offset with respect to the longitudinal direction L, to reduce the length of the compression aperture 223 along the longitudinal direction L, thereby also reducing the length of the bone implant 1 along the longitudinal direction L. Thus, it should be appreciated that the first and second wire segments 101*a* and 101*b* can be flexible. As the length of the compression aperture 223 is decreased along the longitudinal direction, first and second bone fixation-receiving apertures on opposite sides of the compression aperture 223 are also drawn toward each other, thereby compressing the first and second bone fragments of the underlying bone to which the bone implant 1 is attached. For instance, a first bone fixation element inserted through a first one of the apertures 30 and into the bone on a first side of the bone fracture location and a second bone fixation element is inserted through a second one of the apertures 30 on a second side of the fracture location opposite the first side, such that the fracture location is disposed between the first and second bone fixation elements along the longitudinal direction L. The first and second bone fixation elements can further be disposed on opposite sides of the compression aperture 223, such that the compression aperture 223 is thus disposed between the first and second bone fixation elements along the longitudinal direction L. The portions of the first and second wire segments 101*a* and 101*b* that define the compression aperture 223 can be crimped in the select direction, which thereby creates a force that biases the first and second bone fixation elements toward each other. One or more additional bone fixation elements are inserted through one or more respective other apertures 30 and into the underlying bone so as to further attach the bone implant 1 to the underlying bone and secure the bone implant 1 fixed to the bone in the compressed configuration. The first, second, and additional bone fixation elements can be configured as locking screws or compression screws, and can be configured to attach the bone implant 1 to the underlying bone in accordance with any embodiment described herein. The compression aperture 223 can be elongate along a major axis 227 that extends along a direction that is angularly offset, such as perpendicular, to the central axis AA of the bone implant 1. Alternatively, the major axis 227 can be parallel to the central axis AA.

It should further be appreciated that the compression aperture 223 can also be configured as a distraction aperture that is configured to move the first and second bone fragments away from each other. For instance, the portions of the first and second wire segments 101a and 101b that define the aperture 223, for instance at their lateral side walls 38 and 36, respectively, can be crimped along the second direction that is substantially perpendicular to the central axis AA, so as to increase the length of the aperture 223 along the central axis AA, thereby also increasing the length of the bone implant 1 from the proximal end to the distal end along the central axis AA.

Referring now to FIG. 11, the bone implant 1 can include a bone plate 2j constructed in accordance with another embodiment, and can include an implant body 15 that, in turn, includes first and second wire segments 101a and 101b that define respective apertures 30, including the compression aperture 223, in the manner described above with respect to FIG. 10. The bone implant 1 can further include an aperture 32 that is constructed as the second aperture type, and is thus elongate along the longitudinal direction L. The aperture 32 can spaced from the compression aperture 223 along the longitudinal direction L. For instance the aperture 32 can be spaced along the proximal direction or the distal direction from the compression aperture 223. The aperture 32 can be disposed adjacent the compression aperture 223, such that no other apertures extending through the implant body 15 along the transverse direction T are disposed between the aperture 32 and the compression aperture, or the bone implant 1 can define one or more apertures 30 between the aperture 32 and the compression aperture 223.

Thus, during operation, a first bone fixation element inserted through a first one of the apertures 30 and into the bone on a first side of the bone fracture location. A second bone fixation element is inserted through the elongate aperture 32 on a second side of the fracture location opposite the first side, such that the fracture location is disposed between the first and second bone fixation elements along the longitudinal direction L. The first and second bone fixation elements can further be disposed on opposite sides of the compression aperture 223, such that the compression aperture 223 is thus disposed between the first and second bone fixation elements along the longitudinal direction L. The portions of the first and second wire segments 101a and 101b that define the compression aperture 223 can be crimped in the select direction, which thereby creates a force that biases the first and second bone fixation elements toward each other. The second bone fixation element can ride along the elongate aperture 32 as the first and second bone fragments are drawn toward each other. Thus, the elongate aperture 32 can guide the compression of the first and second bone fragments toward each other. The second bone fixation element can then be fixed to the implant body 15 so as to secure the bone implant 1 to the bone. For instance, the second bone fixation element can be configured as a compression screw that compresses the implant body 15 against the underlying bone. Alternatively, the second bone fixation element can be threaded and configured to threadedly engage the implant body 15 in the elongate aperture 32 to secure the bone implant 1 relative to the underlying bone.

The aperture 223 can alternatively be used as a distraction aperture that is configured to move the first and second bone fragments away from each other. For instance, the portions of the first and second wire segments 101a and 101b that define the aperture 223 can be crimped in the second direction that is angularly offset with respect to the central axis AA, which thereby creates a force that biases the first and second bone fixation elements away from each other. The second bone fixation element can ride along the elongate aperture 32 as the first and second bone fragments are drawn toward each other. Thus, the elongate aperture 32 can guide the distraction of the first and second bone fragments away each other. The second bone fixation element can then be fixed to the implant body 15 so as to secure the bone implant 1 to the bone. For instance, the second bone fixation element can be configured as a compression screw that compresses the implant body 15 against the underlying bone. Alternatively, the second bone fixation element can be threaded and configured to threadedly engage the implant body 15 in the elongate aperture 32 to secure the bone implant 1 relative to the underlying bone.

Referring now to FIGS. 12A-B, the bone implant 1 can include a bone plate 2k constructed in accordance with another embodiment, and can include an implant body 15 that, in turn, includes a wire 101 that defines first and second wire segments 101a and 101b in the manner described herein. The bone implant 1 can define a first region 1a that includes a first at least one aperture such as a first plurality of apertures that that extend through the implant body 15. The bone implant 1 can further define a second region 1b that includes a second at least one aperture such as a second plurality of apertures that that extend through the implant body 15. The bone implant 1 can further define a third region 1c that defines a transition region configured to adjust at least one of the length of the implant 1 between the proximal end distal ends 16 and 17, or an angular orientation of at least one of the first plurality of apertures with respect to at least one other one of the apertures of the bone implant.

The first plurality of apertures at the first region 1a can include one or more apertures 30, one or more apertures 32, one or more compression apertures 223, or any alternative aperture as described herein. At least two or more, up to all, of the apertures at the first region 1a of the bone implant 1 can be spaced from each other along the central axis AA, and can define respective central axes that are aligned with each other along the central axis AA. Thus, the first region 1a can be elongate along the central axis AA. The second plurality of apertures at the second region 1b can include one or more apertures 30 as illustrated, or can alternatively define one or more apertures 32, one or more compression apertures 223, or any alternative aperture as described herein. At least two or more, up to all, of the apertures at the second region 1b of the bone implant 1 can be spaced from each other along the second direction that is angularly offset, such as perpendicular, with respect to the central axis AA, and can define respective central axes that are aligned with each other along the second direction.

The first and second wire segments 101a and 101b can extend from the transition region 1c to the second region 1b. The apertures 30 at the second region 1b can be constructed by bending the first wire segment 101a, and thus the wire 101, counterclockwise from a base of the first wire segment 101a toward the central axis AA along a path that can, for instance, be circular and toward the base so as to define a corresponding neck 40. While the second region 1b can define apertures as described herein, it should be appreciated that the second region can define an attachment location having any suitable structure, such as the prongs 20 or the like, configured to attach the implant 1 to bone. The first wire segment 101a can then extend toward the central axis AA from the neck 40 to a second base, for instance along a curved path or any alternatively shaped path. The first wire segment 101a can be bent counterclockwise from the second base of the first wire segment 101a toward the central axis AA along a path that can, for instance, be circular and toward the second base so as to define a corresponding neck 40. This process can be repeated as many times a desired so as to define as many apertures 30 of the first wire segment 101a as desired. The first wire segment 101a can contact the base, and can be attached to the bases in any manner described herein, or can be spaced from the bases at the neck.

The apertures 30 at the second region 1b can further be constructed by bending the second wire segment 101b, and thus the wire 101, clockwise from a base of the second wire segment 101b toward the central axis AA along a path that can, for instance, be circular and toward the base so as to define a corresponding neck 40. The second wire segment 101b can then extend toward the central axis, for instance along a curved path or alternatively shaped path, to a second base. The second wire segment 101b can be bent clockwise from the second base toward the central axis AA along a path that can, for instance, be circular and toward the second base so as to define a corresponding neck 40. This process can be repeated as many times a desired so as to define as many apertures 30 of the second wire segment 101b as desired at the second region 1b. The second wire segment 101b can contact the bases, and can be attached to the bases in any manner described herein, or can be spaced from the bases at the neck.

The bone implant 1 can define the compression aperture 223 to adjust a size and/or shape of at least a portion of the bone implant 1 in the manner described above. The bone implant 1 can further define an adjustment zone 237 at the transition region 1c between the first region 1a and the second region 1b. It is recognized that the second region 1b is spaced from the first region 1a along a first select direction, such as the distal direction, and the first region 1a is spaced from the second region 1b along a second select direction, such as the proximal direction, that is opposite the first select direction. The wire segments 101a and 101b can each include a first portion 128a and 128b, respectively, that extends relative to, for instance from, the first region 1a along a direction that includes the second select direction (e.g., away from the second region 1b) and the lateral direction A away from the central axis AA. Thus, each of the wire segments 101a and 101b can be bent back on itself at the respective first portion 128a and 128b so that it overlaps itself with respect to the lateral direction A. Each of the wire segments 101a and 101b can include a second portion 128c and 128d, respectively, that extends relative to, for instance from, the respective first portion 128a and 128b along a direction that includes the first select direction and the lateral direction A away from the central axis AA. For instance, the second portion 128c and 128d of the first and second wire segments 101a and 101b, respectively, can be curved and convex with respect to the first region 1a.

The adjustment zone 237 can include the first and second portions 128a-d of the first and second wire segments 101a and 101b, and can simulate an accordion structure that can be expanded so as to lengthen the bone implant 13 and contracted so as to shorten the implant 13. Thus, the adjustment zone 237 can be configured to be an expansion zone that increases the length of the implant 1 between the proximal end 16 and the distal end 17 along the central axis AA, and a contraction zone that decreases the length of the implant 1 between the proximal end 16 and the distal end 17 along the central axis AA. For instance, the first and second portions 128a-d can be bent so as to lengthen the implant 1 along the central axis AA. For example, the first portions 128a and 128b of the first and second wire segments 101a and 101b can be redirected so as to be unbent. Further, the second portions 128c and 128d can be redirected so as to extend more linearly. Alternatively, the first and second portions 128a-d can be bent so as to reduce the length of the implant 1 along the central axis AA As discussed above, each of the apertures that extend through the implant body 15, for instance at the first region 1a or the second region 1b, can be at least partially defined by at least one neck that is disposed proximal or distal to the respective aperture. The apertures 30, 223, and 32 of the first region 1a are illustrated as being partially defined by first and second necks 40 and 42. The apertures 30 of the second region 1b are illustrated as being partially defined by respective necks 40. As described above, the necks 40 and 42 can define abutment locations. In accordance with one embodiment, one or more up to all of the necks 40 and 42 do not define attachment zones. Rather, one or more up to all of the necks 40 and 42 at the first region 1a can define abutment zones such that the first and second wire segments 101a and 101b abut but do not attach to each other. One or more up to all of the necks 40 at the first region 1b can define abutment zones such that the first and second wire segments 101a and 101b abut but do not attach to their respective bases so as to define the corresponding apertures 30.

The bone implant 1 can be placed against the bone B such that the first region 1a overlies the second bone fragment SB, the second region 1b overlies the first bone fragment FB, and the transition region 1c overlies the fracture location FL. The wire segments 101a and 101b can be manipulated, for instance bent, at locations proximate to the apertures 30 of the second region 1b, including at regions where the wire segments 101a and 101b define the apertures 30, so as to independently adjust the angle of their respective central axes CA that define a trajectory along which a bone fixation element, such as a bone screw, is to be inserted through the apertures 30 and into the underlying bone. The angle of the central axis CA of one or more up to all of the apertures 30 can be varied relative to an implant plane which runs in a direction perpendicular to the central axis AA of the bone implant 13. Accordingly, the apertures 30 of the second region 1b can be referred to as variable angle apertures that allow the trajectory of bone fixation elements that are inserted through the apertures 30 and into the bone B to be adjusted.

As illustrated at FIG. 12B, the wire 101, and thus the implant body 15, can define an undulating wave shape that changes locations in the transverse direction T as the implant body 15 (perpendicular to the longitudinal and lateral directions) between the proximal end 16 and the distal end 17. For instance, the bone facing surface 19a can have a first plurality of select regions 235a along its length between the proximal and distal ends 17 that are spaced along the inner transverse direction T with respect to a second plurality of select regions 235b along its length. Thus, the first plurality of select regions 235a can be configured to abut the underlying bone, while the second plurality of select regions 235b can be spaced from the bone when the first plurality of select regions 235a abut the underlying bone. Thus, the undulating wave shape minimizes the potential contact of the bone implant 1 on the bone B, for instance at the second plurality of select regions, thereby allowing for improved fluid flow between the bone implant 1 and the outer surface of the bone.

Referring now to FIGS. 13A-C, the bone implant 1 can include a bone plate 21 constructed in accordance with another embodiment, and can include an implant body 15 that, in turn, includes a wire 101 that defines first and second wire segments 101a and 101b in the manner described herein. The bone implant 1 can be generally constructed as described above with respect to the bone plate 2k illustrated in FIGS. 12A-B, and thus can define an adjustment zone 237, which can be an expansion zone or a contraction zone of the type described above. The first portions 128a-b of the wire segments 101a-b can extend relative to, for instance from, the first implant region 1a along the lateral direction A away from the central axis AA, and can further extend along the first select direction (e.g., toward the second implant region 1b). It should thus be appreciated that the wire segments 101a and 101b can be undulated at the transition region 1c, so as to be adjustable, e.g., bended, to lengthen or shorten the implant body 1 between the proximal and distal ends 16 and 17.

Further, as described above, the bone implant 1 can define variable angle apertures 239 that extend through the implant body 15, for instance at the second region 1b, that are configured to receive bone fixation elements, and can be constructed in accordance with another embodiment.

The apertures 239 at the second region 1b can be constructed by bending the first wire segment 101a, and thus the wire 101, along a first counterclockwise path from a base of the first wire segment 101a toward the central axis AA and toward the base so as to define a first aperture 239a and a corresponding neck 40 that defines one end of the first aperture 239a. The path can, for instance, be teardrop-shaped such that the corresponding first aperture 239a is likewise teardrop shaped. The first wire segment 101a can then extend from the base, and thus the neck 40 of the first aperture 239a, along a second clockwise path toward the central axis AA, such as a teardrop-shaped path, so as to define the second aperture 239b. The first wire segment 101a can extend along the counterclockwise path to a second base that can be defined by a surface, such as a laterally innermost surface, of the first wire segment 101a that defines the first aperture 239a, so as to define the neck 40 of the second aperture 239b. The first and second apertures 239a and 239b can be inverted, such that the necks 40 are on opposite sides of the first and second apertures 239a-b. For instance, the necks 40 of the first apertures 239a can be disposed proximal of the first apertures 239a, and the necks 40 of the second apertures 239b can be disposed distal of the second apertures 239b. This process can be repeated as many times as desired so as to produce a desired number of first and second apertures 239a and 239b. While the paths were described herein as being teardrop shaped, it should be appreciated that any suitable alternatively shaped path is envisioned.

The apertures 239 at the second region 1b can be constructed by bending the second wire segment 101b, and thus the wire 101, along a first clockwise path from a base of the second wire segment 101b toward the central axis AA along a path that can, for instance, be teardrop-shaped, and toward the base so as to define a first aperture 239a and a corresponding neck 40 that defines one end of the first aperture 239a. The second wire segment 101a can then extend from the base, and thus the neck 40, of the first aperture 239a, along a second clockwise path toward the central axis AA so as to define a second aperture 239b. The second wire segment 101b can extend along the counterclockwise path to a second base that can be defined by a surface, such as a laterally innermost surface, of the previously-created first wire segment 101a that defines the first aperture 239a, so as to define the neck 40 of the second aperture 239b. This process can be repeated as many times as desired so as to produce a desired number of first and second apertures 239a and 239b. The first and second apertures 239a and 239b can be inverted, such that the necks 40 are on opposite sides of the first and second apertures 239a-b. For instance, the necks 40 of the first apertures 239a can be disposed proximal of the first apertures 239a, and the necks 40 of the second apertures 239b can be disposed distal of the second apertures 239b. This process can be repeated as many times as desired so as to produce a desired number of first and second apertures 239a and 239b. While the paths were described herein as being teardrop shaped, it should be appreciated that any suitable alternatively shaped path is envisioned.

The first and second apertures 239a and 239b can be arranged in respective first and second rows 241a and 241b that extend along the lateral direction and are spaced from each other along the longitudinal direction L. One teardrop shaped aperture 239 in one row forms the start of a teardrop shaped aperture 239 in the other row. The wire 101, for instance at the necks 40 of the teardrop shaped apertures 239 are not fixed together at the abutment points, thereby allowing the wire 101 to be manipulated so as to adjust the angle of the apertures 239 as desired. For example, the wire segments 101a and 101b can be manipulated, for instance bent, at locations proximate to the apertures 239 of the second region 1b, including at regions where the wire segments 101a and 101b define the respective apertures 239 and the necks 40, so as to independently adjust the angle of their respective central axes CA that define a trajectory along which a bone fixation element, such as a bone screw, is to be inserted through the apertures 239 and into the underlying bone. The angle of the central axis CA of one or more up to all of the apertures 239 can be varied relative to an implant plane which runs in a direction perpendicular to the central axis AA of the bone implant 13. Accordingly, the apertures 239 of the second region 1b can be referred to as variable angle apertures that allow the trajectory of bone fixation elements that are inserted through the apertures 30 and into the bone B to be adjusted.

It should be further appreciated that the wire segments 101a and 101b can further be manipulated, for instance bent, at locations proximate to the apertures 239 of the second region 1b, including at regions where the wire segments 101a and 101b define the respective apertures 239 and the necks 40, so as to widen the implant 1 along the lateral direction A, or lengthen the implant 1 along the longitudinal direction L relative to a plane which runs in a direction perpendicular to the central axis AA. However, as the skilled person would understand, when a user manipulates a teardrop shaped aperture 239 in of the first and second rows 241a and 241b the aperture adjacent to it in the other of the first and second rows 241a and 241b may be deformed such that it is no longer usable as a bone fixation element-receiving aperture.

As illustrated in FIG. 13B, and as described above with respect to FIG. 12B, the wire 101, and thus the implant body 15, can define an undulating wave shape that changes locations in the transverse direction T as the implant body 15

(perpendicular to the longitudinal and lateral directions) between the proximal end 16 and the distal end 17. For instance, the bone facing surface 19a can have a first plurality of select regions 235a along its length between the proximal and distal ends 17 that are spaced along the inner transverse direction T with respect to a second plurality of select regions 235b along its length. Thus, the first plurality of select regions 235a can be configured to abut the underlying bone, while the second plurality of select regions 235b can be spaced from the bone when the first plurality of select regions 235a abut the underlying bone. Thus, the undulating wave shape minimizes the potential contact of the bone implant 1 on the bone B, for instance at the second plurality of select regions, thereby allowing for improved fluid flow between the bone implant 1 and the outer surface of the bone.

Alternatively, as illustrated in FIG. 13C, the bone-facing surface 19a of the implant body 15 can be substantially linear between the proximal end 16 and the distal end 17. For instance, the bone facing surface 19a at the first region 1a can be angularly offset with respect to the bone facing surface 19a at the second region 1b. In accordance with one embodiment, the bone facing surface 19a at the second region extends along the outer transverse direction along its length along the distal direction away from the first region 1a.

While the bone implant 1 can be configured as one or more of the bone plates 14a-1, and alternatives thereof, as described above, it should be appreciated that the bone implant 1 can alternatively be constructed as any suitable alternative bone implant. For instance, the bone implant 1 can be configured as an intramedullary nail that is configured to be inserted into a medullary canal of the bone B and fixed to the first and second bone fragments FB and SB in the manner described herein.

Referring now to FIGS. 14A-D generally, a bone implant system can include any of the bone implant assemblies and bone implants, alone or in combination, constructed in accordance with any embodiment described herein, in addition to one or more bone fixation elements 209 that are configured to secure the bone implant 1 to bone. While the bone fixation elements 209 are illustrated as screws, it should be appreciated that the fixation elements can be constructed in accordance with any suitable alternative embodiment. For instance, the bone fixation elements can be configured as bone pins, rivets, staples, and the like. The bone fixation elements are thus configured to be inserted through the apertures 30 and into the bone. It should be appreciated, as described above, that the apertures illustrated in FIGS. 14A-D can be configured as apertures 30, 32, 115, 223, or any alternatively constructed aperture as described herein.

In general, as described above with respect to FIGS. 7A-B, the bone fixation elements 209 can include a head 209a and a shaft 209b that extends out relative to the head along a distal direction, for instance from the head 209a, and is configured to be inserted into the bone such that the head 209a secures the bone implant 1 to the bone. The bone fixation element 209 can further include a neck that is disposed between the head 209a and the shaft 209b. The head 209a can, for instance, compress the bone implant 1 to the bone, or can attach to the bone implant 1 without compressing the bone implant 1 against the bone, thereby providing a locked construct the fixes the implant 1 with respect to movement relative to the bone. The bone fixation elements 209 can be dimensioned as desired. For example, the shaft 209b may have a diameter between and including approximately 1.5 mm and approximately 3.0 mm, and the head 209a may have a diameter or alternative cross-sectional dimension along a direction perpendicular to the central axis of the shaft 209b between 2.0 mm to 4.5 mm. Thus the head 209a can have a greater diameter than the shaft 209b, or can alternatively have a substantially equal diameter with respect to the shaft 209b. The head 209a can further define a socket or alternative driving mechanism configured to engage a driving instrument so as to receive a torsional force from the driving instrument that drives the bone fixation element 209 into the bone. The socket can be faceted to allow the instrument to rotate the fixation element. Suitable socket shapes include, but are not limited to, triangle, square, pentagonal, hexagonal, octagonal and other polygonal shapes, star shaped, and the like.

Referring now to FIG. 14A, the bone fixation element 209 can be configured as a wire 211 of the type described above that is helically wound about a central axis 221 so as to define successive loops 220 that are spaced from each other along the central axis 221 so as to define the head 209a and the shaft 209b. The loops 220 can abut each other, such that each loop defines a thread 221. The loops 220 are configured to receive an unthreaded inner surface 34 of the first and second wire segments 101a-b, which is shaped so as to nest between adjacent loops 220. Thus, rotation of the bone fixation element 209 with respect to the bone implant 1 in a first direction causes the inner surfaces 34 to ride between successive loops 220, thereby driving the head 209a into the aperture 30, and thus driving the shaft 209b into the underlying bone. Rotation of the bone fixation element 209 with respect to the bone implant 1 in a second direction opposite the first direction causes the inner surfaces 34 to ride between successive loops 220, thereby driving the head 209a out of the aperture 30, and thus driving the shaft 209b out of the underlying bone.

Referring now to FIG. 14B, the bone fixation element 209 can alternatively define threads 221a formed in the outer surface of the head 209a, and threads 221b formed in the outer surface of the shaft 209b. At least a portion up to an entirety of the outer surface of the head 209a can be tapered, for instance conically tapered, toward the central axis 221 as it extends along a direction toward the shaft 209b. Alternatively or additionally, at least a portion up to an entirety of the outer surface of the head 209a can extend substantially parallel to the central axis 221 as it extends along a direction toward the shaft 209b. The inner surface 34 can further be threaded. For instance, at least a portion up to an entirety of the inner surface 34 can be tapered, for instance conically tapered, toward the central axis CA of the aperture 30 as it extends along a direction from the outer surface 19b toward the bone facing surface 19a. Alternatively or additionally, at least a portion up to all of the inner surface 34 can be extend substantially parallel to the central axis CA of the aperture 30 as it extends along a direction from the outer surface 19b toward the bone facing surface 19a. The threaded outer surface 221a of the head 209a is sized so as to threadedly mate with the threaded inner surface 34. Thus, rotation of the bone fixation element 209 with respect to the bone implant 1 in a first direction drives the head 209a into the aperture 30, and thus drives the threaded shaft 209b into the underlying bone. Rotation of the bone fixation element 209 with respect to the bone implant 1 in a second direction opposite the first direction drives the head out of the aperture 30, and thus drives the shaft 209b out of the underlying bone.

Referring now to FIG. 14C, as described above, the head 209a can be configured to compress the bone implant 1 against the underlying bone. For instance, the head 209a can be unthreaded and the inner surface 34 can further be unthreaded. The shaft 209b can be threaded in the manner described above. It should be appreciated that the outer surface of the head 209a and the inner surface 34 of the wire segments 101a and 101b can be shaped as desired, and can be shaped so as to correspond with each other. Accordingly, a majority up to an entirety of the inner surface 34 can be configured to abut the outer surface of the head 209a. In accordance with one embodiment, the outer surface of the head 209a can be convex and the inner surface 34 can be concave, such that the head 209a nests in the inner surface 34. It should be appreciated, of course, that the outer surface of the head 209a can be concave and the inner surface 34 can be convex, such that the inner surfaces 34 are configured to nest in the outer surface of the head 209a. During operation, the shaft 209b is inserted through the aperture 30, until the shaft 209b is inserted into the bone. The shaft 209b can be further inserted into the bone, for instance threadedly or otherwise, until the outer surface of the head 209a contacts the inner surface 34 of the first and second wire segments 101a and 101b. Further insertion of the shaft 209b into the bone thus causes the outer surface of the head 209a to compress the first and second wire segments 101a-b against the bone 30.

Referring now to FIG. 14D, the head 209a can define first and second ridges 224a and 224b that are spaced from each other along the distal direction, so as to define a groove 207 disposed between the first and second ridges 224a and 224b. The groove 207 can be recessed toward the central axis 221 with respect to the ridges 224a-b. The groove 207, for instance, can be curved and convex, and can further be unthreaded, and can define a cross-sectional dimension slightly less than the distances that the threaded inner surface 34 are spaced apart from each other. The first ridge 224a can extend further out from the central axis 221 than the first ridge 224b, though it should be appreciated that the first and second ridges 224a-b can extend out a substantially equal distance from the central axis 221. The head 209a can be threaded at a location distal of the groove 207. For instance, the second ridge 224b can be threaded. The inner surfaces 34 can also be threaded, and configured to mate with the threads of the second ridge 224b.

The outer surface of the head 209a can define threads 221 that are configured mate with the threaded inner surface 34. During operation, the shaft 209b, which can be threaded, is inserted through the aperture 30 and into the bone. The bone fixation element 209 can be rotated or translated so as to drive the shaft 209b into the bone until the threaded second ridge 224b abuts the inner surface 34, at which point the bone fixation element 209 is rotated in a first direction so as to cause the threaded second ridge 224b to threadedly mate with the threaded inner surfaces 34. Because the second ridge 224b has a diameter greater than the distance that the inner surfaces 34 are spaced from each other, for instance along the lateral direction A, the second ridge 224b can drive the wire segments 101a-b to spread apart from each other so that the threaded second ridge 224b threadedly mates with the threaded inner surfaces 34. The bone fixation element 209 can be further rotated in the first direction until the groove 207 is aligned with the inner surfaces 34, at which point a spring force from the resilient flexible wire segments 101a-b causes the wire segments 101a-b to draw toward each other and seat in the groove 207. The groove 207 can loosely capture the inner surface 34 between the first and second ridges 224a and 224b, such that the bone fixation element is movable with respect to the bone implant 1. Accordingly, at least one of the bone fragments of the bone is able to move with respect to the other bone fragment, otherwise known as micromotion between the bone fragments, at the fracture location which can promote healing of the bone fracture.

The bone implants 1, bone implant assemblies, and bone implant systems of the type described herein can have the same and/or different dimensions may be part of a kit, and housed in an openable casing for transportation, storage, ease of selection in the operating room, etc. The user, such as a surgeon or a vet, may select any bone implant according to type of bone, fracture, etc., to be stabilized for bone healing.

The bone implant 1 can be used to support bone healing. One or a combination of the bone plates 2a-2l can be used according to the type of surgical operation to be performed. The bone implants 1 can of course be used in conjunction with other traditional bone implants, if necessary. The user, such a surgeon or veterinary practitioner, having selected the bone implant according to the surgical procedure to be performed, may take any necessary step to perform the surgical procedure in which the bone implant is fixed to the bone to stabilize the fracture and support bone healing.

In the operating room, having prepared the bone for fixation and selected an appropriate implant according to the type of bone, type of fracture, etc. If desired, the user can bend the bone implant 1 to more accurately match the shape of the bone. The bone implant 1 can be easily deformed in all directions as described above. The user will then reduce the bone fracture and will then insert bone fixation elements into the apertures to stably fix to the bone fragments with respect to each other.

The user may vary the angle of insertion of a fixation element through the apertures of the bone implant 1. In one embodiment, this may be through engaging a fixation element at angle relative to the aperture using conventional variable angle techniques. For instance, an insert can be inserted into one of the apertures so as to threadedly support the bone fixation elements at a plurality of angles with respect to the central axis of the aperture. Another option is to bend the one or both of the wire segments so as to adjust the orientation of the central axis of the aperture itself, as described above. To support the varying of the angle of the central axis relative to the implant plane, drill guides may be preloaded in the individual holes. The drill guides may be discreet drill guides allowing one aperture to be adapted at a time independent from other apertures.

The bone implants 1 can be fabricated by bending one or more wire segments in a predetermined manner. Examples of suitable materials for the wires described herein include steel, titanium, titanium alloys, such as nitinol and Gummetal®, magnesium, glass metals, plastics, fiber reinforced plastics, PEEK and bioresorable wire. Other suitable materials are of course possible. The wire 101 can have a diameter in a range from 0.2 mm to 5 mm. The rigidity and strength of the implant may increase as the diameter gets larger. In one embodiment, the wire has a diameter of 0.6 mm. In another embodiment, the wire has a diameter of 1.25 mm. In another embodiment, the wire has a diameter of 1.5 mm. In a further embodiment, the wire has a diameter of 1.8 mm. As the skilled person would understand, other diameters are of course possible.

To manufacture a bone implant, the wire 101 can be bent by a wire bending machine into a predetermined shape to form an implant precursor. The shape of the wire is selected according to the type of bone for which the implant is to be used. The implant precursor is then passed into a pressing device. In the press, optionally, a three dimensional shape may be formed by bending the wire over a suitable mold. Portions of the implant precursor are may optionally be pressed around an aperture forming structures. For example, the aperture forming structure may have a thread formed thereon provided to form a thread in the aperture. Subsequently, the implant precursor is passed into a further device for fixing the abutment points together to form the bone implant of any type as described herein. The implant can then be further processed as necessary. For example, the implant may be heated and pressed to flatten various surfaces of the wire segments, for instance the bone facing and opposed outer surfaces. In another example, the implant 1 may be coated with, for example, diamond like carbon. In another example, the bone implant 1 may be chemically processed using, for example, anodization, electropolishing, etc. Since there is minimal additional processing in terms of milling, drilling, cutting, etc., the bone implant 1 may be manufactured with minimal waste material.

It will of course be understood that this description is by way of example only; alterations and modifications may be made to the described embodiment without departing from the scope of the invention as defined in the claims.

The invention claimed is:

1. A bone implant elongate along a longitudinal axis that is oriented along a longitudinal direction, the bone implant comprising:
   an implant body defining a proximal end and a distal end spaced from the proximal end along the longitudinal direction, the implant body including first and second side wire segments that are spaced from each other along a lateral direction so as to define at least one aperture extending through the implant body, the lateral direction substantially perpendicular to the longitudinal direction, the first and second side wire segments attached to each other at least at one end of the at least one aperture,
   wherein at least one of the first and second side wire segments is bent so as to singly define at least one additional aperture extending through the implant body, the at least one aperture is located at one of the proximal and distal ends of the implant body, the at least one additional aperture is located at the other of the proximal and distal ends of the implant body, and a maximum dimension of the implant body measured along the longitudinal direction is greater than a maximum dimension of the implant body measured along the lateral direction.

2. The bone implant as recited in claim 1, wherein the first and second side wire segments define a neck at the one end of the at least one aperture, and the first and second side wire segments are attached to each other at the neck.

3. The bone implant as recited in claim 2, wherein the first and second side wire segments are at least one of welded, soldered, or glued to each other at the neck.

4. The bone implant as recited in claim 1, wherein the end of the at least one aperture is a first end, and the first and second side wire segments further attach to each other at a second end of the at least one aperture that is opposite the first end.

5. The bone implant as recited in claim 4, wherein the first and second side wire segments define a first neck at the first end, the first and second side wire segments define a second neck at the second end, and the first and second side wire segments attach to each other at each of the first and second necks.

6. The bone implant as recited in claim 1, wherein each of the first and second side wire segments defines an inner surface that faces the inner surface of the other of the first and second side wire segments, and the inner surfaces are threaded at the at least one aperture.

7. The bone implant as recited in claim 1, wherein the at least one aperture is substantially circular.

8. The bone implant as recited in claim 1, wherein the at least one aperture is elongate along the longitudinal axis.

9. The bone implant as recited in claim 1, wherein the at least one of the first and second side wire segments is bent at the distal end so as to singly define the at least one additional aperture at the distal end, the at least one additional aperture configured to receive a bone fixation element so as to attach the bone implant to bone.

10. The bone implant as recited in claim 1, wherein the at least one of the first and second side wire segments is bent around itself at the proximal end so as to singly define the at least one additional the distal end so as to singly define the at least one additional aperture at the distal end, the at aperture at the proximal end, the at least one additional aperture at the proximal end configured to receive a bone fixation element so as to attach the bone implant to bone.

11. The bone implant as recited in claim 1, wherein the first and second side wire segments are integral and monolithic with each other to form a single wire.

12. The bone implant as recited in claim 1, wherein the first and second side wire segments further define a compression aperture that extends through the implant body, the compression aperture is located between the at least one aperture and the at least one additional aperture along the longitudinal direction, and the first and second side wire segments are configured to be crimped at the compression aperture so as to decrease the maximum dimension of the bone implant along the longitudinal direction.

13. The bone implant as recited in claim 1, wherein the at least one aperture defines a central axis, and the first and second side wire segments are configured to be bent so as to adjust an angle of the central axis with respect to the longitudinal axis.

14. The bone implant as recited in claim 1, wherein the first and second side wire segments are mirror images of each other.

15. The bone implant as recited in claim 1, wherein the implant body defines a bone facing surface and an outer surface that is spaced from the bone facing surface, and each of the first and second side wire segments at least partially defines an attachment location configured to attach to bone.

16. The bone implant as recited in claim 15, wherein the at least one aperture is a first aperture, the at least one additional aperture is a second aperture, and the attachment location comprises a third aperture defined by the first and second side wire segments.

17. The bone implant as recited in claim 16, wherein the first and third apertures are spaced from each other by a neck that is defined at a location between the first and third apertures, wherein at least one of the first and second side wire segments extends toward the other of the first and second side wire segments at the neck.

18. The bone implant as recited in claim 1, wherein the at least one aperture is a first aperture, the at least one additional aperture is a second aperture, the first and second side wire segments define respective first and second side walls that are spaced from each other so as to define the first aperture and a third aperture each configured to receive a bone fixation element so as to attach the bone implant to bone, and the first and second side walls extend continuously from a first end of the first aperture to a second end of the third aperture, and the first and third apertures are disposed between the first and second ends.

19. A bone implant elongate along a longitudinal axis, the bone implant comprising:
an implant body including first and second side wire segments that define respective first and second side walls that are spaced from each other so as to define first and second apertures each configured to receive a bone fixation element so as to attach the bone implant to bone, wherein the first and second side walls extend continuously from a first end of the first aperture to a second end of the second aperture, and the first and second apertures are disposed between the first and second ends,
wherein the first and second side wire segments define a first neck at one end of the first aperture and a second neck at one end of the second aperture, the first and second side wire segments abut each other at the first and second necks, the first and second side wire segments define a third neck at the other end of the first aperture, and, at the first and third necks, the first and second side wire segments both extend along a shared plane that includes a longitudinal direction and a lateral direction.

20. The bone implant as recited in claim 19, wherein the first neck is at the first end, and the second neck is at the second end.

21. The bone implant as recited in claim 20, wherein the first and second side walls are attached to each other at one or both of the first neck or the second neck.

22. The bone implant as recited in claim 20, wherein the first and second side walls are at least one of welded, soldered, or glued at the first neck or the second neck.

23. The bone implant as recited in claim 19, wherein each of the first and second side walls defines an inner surface that faces the inner surface of the other of the first and second side walls so as to define at least one of the first and second apertures, and the inner surfaces are threaded at the at least one of the first and second apertures.

24. The bone implant as recited in claim 19, wherein the first and second apertures are spaced from each other by at least one of the first and second necks, the at least one of the first and second necks is defined at a location between the first and second apertures, and at least one of the first and second side wire segments extends toward the other of the first and second side wire segments at the at least one of the first and second necks.

25. The bone implant as recited in claim 19, wherein, at the second neck, 1) a first portion of the first side wire segment extends toward a first portion of the second side wire segment substantially along the plane, and 2) the first portion of the second side wire segment extends toward the first portion of the first side wire segment substantially along the plane.

26. A bone implant system comprising:
a bone implant elongate along a longitudinal axis that is oriented along a longitudinal direction, the bone implant defining a proximal end and a distal end spaced from the proximal end along the longitudinal direction, the bone implant comprising an implant body including first and second side wire segments that are spaced from each other along a lateral direction so as to define at least one aperture extending through the implant body, the lateral direction substantially perpendicular to the longitudinal direction, the first and second side wire segments attached to each other at one end of the at least one aperture, wherein at least one of the first and second side wire segments is bent so as to singly define at least one additional aperture extending through the implant body, the at least one aperture is located at one of the proximal and distal ends of the implant body, the at least one additional aperture is located at the other of the proximal and distal ends of the implant body, and a maximum dimension of the implant body measured along the longitudinal direction is greater than a maximum dimension of the implant body measured along the lateral direction; and
a bone fixation element configured to extend through the at least one additional aperture and into a bone so as to attach the bone implant to the bone.

27. A bone implant system comprising:
a bone implant elongate along a longitudinal axis, the bone implant comprising an implant body including first and second side wire segments that define respective first and second side walls that are spaced from each other so as to define first and second apertures each configured to receive a bone fixation element so as to attach the bone implant to bone, wherein the first and second side walls extend continuously from a first end of the first aperture to a second end of the second aperture, the first and second apertures are disposed between the first and second ends, the first and second side wire segments define a first neck at one end of the first aperture and a second neck at one end of the second aperture, the first and second side wire segments are attached to each other at the first and second necks, the first and second side wire segments define a third neck at the other end of the first aperture, and, at the first and third necks, the first and second side wire segments both extend along a shared plane that includes a longitudinal direction and a lateral direction; and
a bone fixation element configured to extend through at least one of the first or second apertures and into a bone so as to attach the bone implant to the bone.

* * * * *